(12) United States Patent
Iwasa et al.

(10) Patent No.: US 11,445,726 B2
(45) Date of Patent: Sep. 20, 2022

(54) PYRIDINIUM SALT AND PEST CONTROL AGENT

(71) Applicant: Nippon Soda Co., Ltd., Tokyo (JP)

(72) Inventors: Takao Iwasa, Odawara (JP); Katsunori Tanaka, Odawara (JP); Atsuko Nabeta, Tokyo (JP); Riho Taguchi, Odawara (JP); Kotaro Shibayama, Odawara (JP); Hiroto Suzuki, Odawara (JP); Rie Sakamoto, Tokyo (JP); Miho Takahashi, Odawara (JP); Tsuyoshi Hoya, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 16/764,253

(22) PCT Filed: Nov. 27, 2018

(86) PCT No.: PCT/JP2018/043554
§ 371 (c)(1),
(2) Date: May 14, 2020

(87) PCT Pub. No.: WO2019/107348
PCT Pub. Date: Jun. 6, 2019

(65) Prior Publication Data
US 2020/0275655 A1 Sep. 3, 2020

(30) Foreign Application Priority Data
Dec. 1, 2017 (JP) .............................. JP2017-231998

(51) Int. Cl.
| | | |
|---|---|---|
| *A01N 43/40* | (2006.01) | |
| *A01N 43/54* | (2006.01) | |
| *A01N 43/56* | (2006.01) | |
| *A01N 43/60* | (2006.01) | |
| *A01N 43/76* | (2006.01) | |
| *A01N 43/78* | (2006.01) | |
| *A01N 43/82* | (2006.01) | |
| *C07D 213/89* | (2006.01) | |
| *C07D 401/12* | (2006.01) | |
| *C07D 405/12* | (2006.01) | |
| *C07D 409/12* | (2006.01) | |
| *C07D 413/12* | (2006.01) | |
| *C07D 417/12* | (2006.01) | |

(52) U.S. Cl.
CPC ............. *A01N 43/40* (2013.01); *A01N 43/54* (2013.01); *A01N 43/56* (2013.01); *A01N 43/60* (2013.01); *A01N 43/76* (2013.01); *A01N 43/78* (2013.01); *A01N 43/82* (2013.01); *C07D 213/89* (2013.01); *C07D 401/12* (2013.01); *C07D 405/12* (2013.01); *C07D 409/12* (2013.01); *C07D 413/12* (2013.01); *C07D 417/12* (2013.01)

(58) Field of Classification Search
CPC .. C07D 401/12; C07D 405/12; C07D 409/12; C07D 413/12; C07D 417/12
See application file for complete search history.

(56) References Cited

U.S. PATENT DOCUMENTS

| | | | |
|---|---|---|---|
| 4,013,669 | A | 3/1977 | Parsons |
| 4,138,548 | A | 2/1979 | Parsons |
| 2011/0301355 | A1 | 12/2011 | Miyashita et al. |

FOREIGN PATENT DOCUMENTS

| | | |
|---|---|---|
| GB | 1 419 377 | 12/1975 |
| JP | 48-077026 A | 10/1973 |

(Continued)

OTHER PUBLICATIONS

International Search Report dated Feb. 12, 2019 in PCT/JP2018/043554, with English translation.

(Continued)

*Primary Examiner* — Erich A Leeser
(74) *Attorney, Agent, or Firm* — Foley & Lardner LLP

(57) ABSTRACT

A compound represented by formula (I) or formula (II):

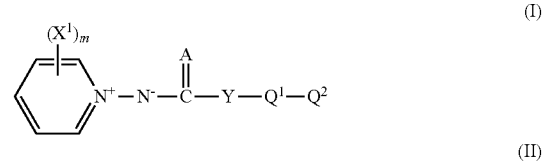

wherein, A represents an oxygen atom or a sulfur atom; $X^1$ represents a halogeno group, a substituted or unsubstituted $C_{1-6}$ alkyl group and so on; m represents the number of $X^1$ and is any integer of 0 to 5; any two of $X^1$ may be bound together to form a bivalent hydrocarbon group; Y represents a single bond or a substituted or unsubstituted $C_{2-6}$ alkenylene group; $Q^1$ represents a substituted or unsubstituted $C_{6-10}$ arylene group or a substituted or unsubstituted 6- to 10-membered heteroarylene group; $Q^2$ represents a substituted or unsubstituted $C_{6-10}$ aryl group or a substituted or unsubstituted 5- to 6-membered heteroaryl group; $Z^{q-}$ represents a counter ion; and q represents a valence of the counter ion and is 1 or 2.

5 Claims, No Drawings

(56) References Cited

FOREIGN PATENT DOCUMENTS

| JP | 04-338387 A | 11/1992 |
|----|----|----|
| WO | WO 2007/015533 A1 | 2/2007 |
| WO | WO-2020/241614 A1 | 12/2020 |
| WO | WO-2020/241632 A1 | 12/2020 |

OTHER PUBLICATIONS

Office Action dated Dec. 24, 2019, in TW 107142602, with English translation.
Abramovitch et al., "Photolytic Generation of N-Acylnitrenium Ions Under Neutral Conditions: Synthesis of Polycyclic Lactams," Heterocycles, 1994, 37(3):1463-1466.
Gangapuram et al., "Synthesis and Biological Evaluation of Substituted N-[3-(1H-Pyrrol-1-yl)methyl]-1,2,5,6-tetrahydropyridin-1-yl]benzamide/benzene Sulfonamides as Anti-Inflammatory Agents," Arch. Pharm. Chern. Life Sci., 2014, 347:360-369.
Guzel et al., "Carbonic anhydrase inhibitors. Synthesis of 2,4,6-trimethylpyridinium derivatives of 2-(hydrazinocarbonyl)-3-aryl-1H-indole-5-sulfonamides acting as potent inhibitors of the tumor-associated isoform IX and XII," Bioorganic & Medicinal Chemistry Letters, 2009, 19:2931-2934.
Yeung et al., "Synthesis of N-[[Substituted-phenyl)carbonyl]amino]1,2,3,6-tetrahydropyridines with Analgesic and Hyperglycemic Activity," J. Med. Chem., 1982, 25:720-723.
Guest et al., "Synthesis and Biological Activity of 3-(N-Substituted Pyridinium-4-Thiomethyl)-7alpha-Formamido Cephalosporins," The Journal of Antibiotics, 1993, 64(8):1279-1288.
International Search Report dated Aug. 11, 2020 in PCT/JP2020/020665, with English translation.
International Search Report dated Jul. 28, 2020 in PCT/JP2020/020719, with English translation.
Jezierska et al., "Synthesis, X-ray Crystallography and Computer-Aided Design Study of 5-Amino-3-methylisoxazole-4-carboxylic Acid N-2,4,6-Trimethylpyridinium)amide Chlorate(VII) Salt and Its Analogues," Polish J. Chem., 2003, 77:1461-1471.
Kakehi et al., "Preparation of New Nitrogen-Bridged Heterocycles. 43. Synthesis and Reaction of 4aH-Pyrido[1,2-3][1,3,4]thiadiazepine Derivatives," J. Org. Chem., 1997, 62:7788-7793.
Kise et al., "Mesomorphic Properties of N-4-Ethylpyridinio)-4-Alkoxybenzamidates: Ylide as a Liquid Crystal," Chemistry Letters, 1978, 11:1235-1238.
Mochona et al., "Synthesis and Anti-Inflammatory Activities of N-Benzoylamino-1,2,3,6-Tetrahydropyridine analogs," Drugs Under Experimental and Clinical Research, 2003, 29(4):131-140.
STN Registry file, May 7, 2004, RN 680623-06-7, 3 pages.
STN Registry file, Nov. 16, 1984, RN 62088-48-6, 3 pages.
STN Registry File, Nov. 16, 1984, RN 62088-50-0, 3 pages.
Yeung et al., "Synthesis of N-Carbonylamino)-1,2,3,6-tetrahydropyridines with Analgesic, Antiinflammatory, and Hyperglycemic Activity," J. Med. Chem., 1982, 25:191-195.
Office Action dated Aug. 2, 2022 in JP 2019-557234, with English translation.

PYRIDINIUM SALT AND PEST CONTROL AGENT

BACKGROUND OF THE INVENTION

Field of the Invention

The present invention relates to a pyridinium salt and a pest control agent. More specifically, the present invention relates to a pyridinium salt which has excellent insecticidal activity and/or acaricidal activity, is excellent in safety and can be synthesized in an industrially favorable manner, and a pest control agent containing this pyridinium salt as an active ingredient.

The present application is the U.S. National Stage of PCT/JP2018/043554, filed Nov. 27, 2018, which claims priority on Japanese Patent Application No. 2017-231998, filed in Japan on Dec. 1, 2017, the content of which is incorporated herein by reference.

Description of the Related Art

Various compounds having insecticidal/acaricidal activities have been proposed. In order to put such a compound to practical use as an agricultural chemical, it is required not only to have sufficiently high efficacy, but also to be difficult to cause drug resistance, not to cause phytotoxicity to plants or soil pollution, and to have low toxicity to livestock and fish, or the like.

Incidentally, Patent Document 1 discloses a compound represented by formula (A) having acaricidal activity, and the like.

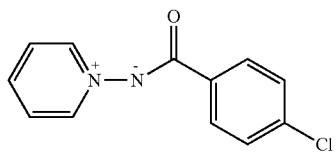

(A)

Further, Non-Patent Document 1 discloses a compound represented by formula (B) having analgesic activity, and the like.

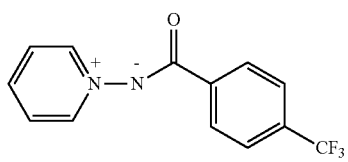

(B)

PRIOR ART DOCUMENTS

Patent Document

[Patent Document 1] U.S. Pat. No. 4,138,548

Non-Patent Document

[Non-Patent Document 1] Journal of Medicinal Chemistry, 1982, vol. 25, p 720-723

SUMMARY OF THE INVENTION

Problems to be Solved by the Invention

An object of the present invention is to provide a pyridinium salt which is excellent in pest control activity, in particular, insecticidal activity and/or acaricidal activity, excellent in safety and can be synthesized in an industrially favorable manner. Another object of the present invention is to provide a pest control agent, an insecticidal or acaricidal agent, an ectoparasite control agent, or an endoparasite control- or exterminating agent containing a pyridinium salt as an active ingredient.

Means for Solving the Problem

As a result of intensive studies in order to solve the above problems, the present invention including the following embodiments has been completed.

[1] A compound represented by formula (I) or formula (II):

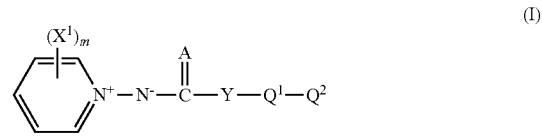

(I)

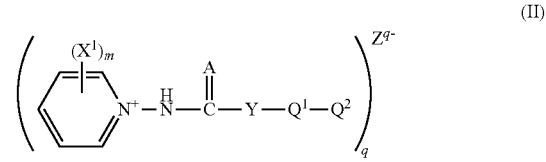

(II)

wherein,

A represents an oxygen atom or a sulfur atom;

$X^1$ represents a halogeno group, a substituted or unsubstituted $C_{1-6}$ alkyl group, a substituted or unsubstituted $C_{2-6}$ alkenyl group, a substituted or unsubstituted $C_{2-6}$ alkynyl group, a hydroxyl group, a substituted or unsubstituted $C_{1-6}$ alkoxy group, a substituted or unsubstituted $C_{2-6}$ alkenyloxy group, a substituted or unsubstituted $C_{2-6}$ alkynyloxy group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkylsulfonyloxy group, an amino group, a substituted or unsubstituted $C_{1-6}$ alkylamino group, a substituted or unsubstituted $C_{3-8}$ cycloalkyl group, a substituted or unsubstituted $C_{3-8}$ cycloalkyloxy group, a substituted or unsubstituted $C_{6-10}$ aryl group, a substituted or unsubstituted $C_{6-10}$ aryloxy group, a substituted or unsubstituted 5- to 6-membered heteroaryl group, a substituted or unsubstituted 5- to 6-membered heteroaryloxy group, a pentafluorosulfanyl group, a nitro group or a cyano group;

m represents the number of $X^1$ and is any integer of 0 to 5;

any two of $X^1$ may be bound together to form a bivalent hydrocarbon group;

Y represents a single bond or a substituted or unsubstituted $C_{2-6}$ alkenylene group;

$Q^1$ represents a substituted or unsubstituted $C_{6-10}$ arylene group or a substituted or unsubstituted 6- to 10-membered heteroarylene group;

$Q^2$ represents a substituted or unsubstituted $C_{6-10}$ aryl group or a substituted or unsubstituted 5- to 6-membered heteroaryl group;

$Z^{q-}$ represents a counter ion; and q represents a valence of the counter ion and is 1 or 2.

[2] A pest control agent containing at least one compound selected from the compounds according to the above [1] as an active ingredient.

[3] An insecticidal or acaricidal agent containing at least one compound selected from the compounds according to the above [1] as an active ingredient.

[4] An ectoparasite control agent containing at least one compound selected from the compounds according to the above [1] as an active ingredient.

[5] An endoparasite control agent or exterminating agent containing at least one compound selected from the compounds according to the above [1] as an active ingredient.

Effects of the Invention

The pyridinium salt of the present invention has a function of controlling pests which are problematic in terms of agricultural crops and hygiene. A control agent containing the pyridinium salt of the present invention can effectively control pests, particularly agricultural pests and mites and ticks at a lower concentration, and can also effectively control ectoparasites and endoparasites that may harm humans and animals.

DETAILED DESCRIPTION OF THE INVENTION

A pyridinium salt of the present invention is a compound (inner salt) represented by formula (I) or a compound (intermolecular salt) represented by formula (II). An inner salt is a compound having a cation center and an anion center in one molecule, that is, a zwitterion. An intermolecular salt is a compound formed by ion association of a cation and an anion, that is, an ion pair.

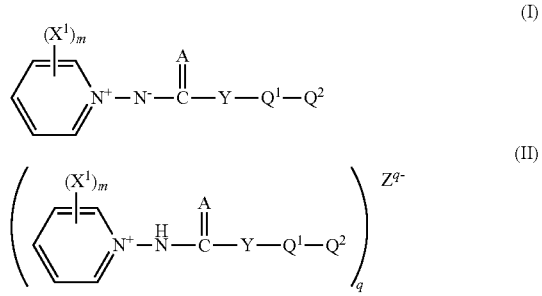

Here, the term "unsubstituted" means that it is composed only of a group which becomes a mother nucleus. When it is described only by the name of the group which becomes the mother nucleus without being described as "substituted", it means "unsubstituted" unless otherwise stated.

On the other hand, the term "substituted" means that any hydrogen atom of the group which is to become the mother nucleus is substituted with a group (substituent) having the same or different structure as that of the mother nucleus. Therefore, a "substituent" is another group bonded to the group which becomes the mother nucleus. The number of substituents may be one, or two or more. Two or more substituents may be the same or different.

The terms "$C_{1-6}$" and the like mean that the number of carbon atoms in the group which becomes the mother nucleus is 1 to 6, and so on. The number of carbon atoms does not include the number of carbon atoms present in the substituent. For example, a butyl group having an ethoxy group as a substituent is classified as a $C_2$ alkoxy $C_4$ alkyl group.

A "substituent" is not particularly limited as long as it is chemically acceptable and has the effects of the present invention. Hereinafter, groups which can be a "substituent" are exemplified.

A $C_{1-6}$ alkyl group such as a methyl group, an ethyl group, an n-propyl group, an i-propyl group, an n-butyl group, an s-butyl group, an i-butyl group, a t-butyl group, an n-pentyl group, and an n-hexyl group;

a $C_{2-6}$ alkenyl group such as a vinyl group, a 1-propenyl group, a 2-propenyl group (allyl group), a 1-butenyl group, a 2-butenyl group, a 3-butenyl group, a 1-methyl-2-propenyl group, and a 2-methyl-2-propenyl group;

a $C_{2-6}$ alkynyl group such as an ethynyl group, a 1-propynyl group, a 2-propynyl group, a 1-butynyl group, a 2-butynyl group, a 3-butynyl group, and a 1-methyl-2-propynyl group;

a $C_{3-8}$ cycloalkyl group such as a cyclopropyl group, a cyclobutyl group, a cyclopentyl group, a cyclohexyl group, and cubanyl group;

a $C_{6-10}$ aryl group such as a phenyl group and a naphthyl group;

a $C_{6-10}$ aryl $C_{1-6}$ alkyl group such as a benzyl group and a phenethyl group;

a 3- to 6-membered heterocyclyl group;

a 3- to 6-membered heterocyclyl $C_{1-6}$ alkyl group;

a hydroxyl group;

a $C_{1-6}$ alkoxy group such as a methoxy group, an ethoxy group, an n-propoxy group, an i-propoxy group, an n-butoxy group, an s-butoxy group, an i-butoxy group, and a t-butoxy group;

a $C_{2-6}$ alkenyloxy group such as a vinyloxy group, an allyloxy group, a propenyloxy group, and a butenyloxy group;

a $C_{2-6}$ alkynyloxy group such as an ethynyloxy group and a propargyloxy group;

a $C_{6-10}$ aryloxy group such as a phenoxy group and a naphthoxy group;

a $C_{6-10}$ aryl $C_{1-6}$ alkoxy group such as a benzyloxy group and a phenethyloxy group;

a 5- to 6-membered heteroaryloxy group such as a thiazolyloxy group and a pyridyloxy group;

a 5- to 6-membered heteroaryl $C_{1-6}$ alkyloxy group such as a thiazolylmethyloxy group and a pyridylmethyloxy group;

a formyl group;

a $C_{1-6}$ alkylcarbonyl group such as an acetyl group and a propionyl group;

a formyloxy group;

a $C_{1-6}$ alkylcarbonyloxy group such as an acetyloxy group and a propionyloxy group;

a $C_{6-10}$ arylcarbonyl group such as a benzoyl group;

a $C_{1-6}$ alkoxycarbonyl group such as a methoxycarbonyl group, an ethoxycarbonyl group, an n-propoxycarbonyl group, an i-propoxycarbonyl group, an n-butoxycarbonyl group and a t-butoxycarbonyl group;

a $C_{1-6}$ alkoxycarbonyloxy group such as a methoxycarbonyloxy group, an ethoxycarbonyloxy group, an n-propoxycarbonyloxy group, an i-propoxycarbonyloxy group, an n-butoxycarbonyloxy group and a t-butoxycarbonyloxy group;

a carboxyl group;

a halogeno groups such as a fluoro group, a chloro group, a bromo group, and an iodo group;

a $C_{1-6}$ haloalkyl group such as a chloromethyl group, a chloroethyl group, a trifluoromethyl group, a 1,2-dichloro-n-propyl group and a 1-fluoro-n-butyl group;

a $C_{2-6}$ haloalkenyl group such as a 2-chloro-1-propenyl group and a 2-fluoro-1-butenyl group;

a $C_{2-6}$ haloalkynyl group such as a 4,4-dichloro-1-butynyl group, a 4-fluoro-1-pentynyl group, and a 5-bromo-2-pentynyl group;

a $C_{1-6}$ haloalkoxy group such as a trifluoromethoxy group, a 2-chloro-n-propoxy group, and a 2,3-dichlorobutoxy group;

a $C_{2-6}$ haloalkenyloxy group such as a 2-chloropropenyloxy group and a 3-bromobutenyloxy group;

a $C_{1-6}$ haloalkylcarbonyl group such as a chloroacetyl group, a trifluoroacetyl group and a trichloroacetyl group;

an amino group;

a $C_{1-6}$ alkyl-substituted amino group such as a methylamino group, a dimethylamino group and a diethylamino group;

a $C_{6-10}$ arylamino group such as an anilino group and a naphthylamino group;

a $C_{6-10}$ aryl $C_{1-6}$ alkylamino group such as a benzylamino group and a phenethylamino group;

a formylamino group;

a $C_{1-6}$ alkylcarbonylamino group such as an acetylamino group, a propanoylamino group, a butyrylamino group and an i-propylcarbonylamino group;

a $C_{1-6}$ alkoxycarbonylamino group such as a methoxycarbonylamino group, an ethoxycarbonylamino group, an n-propoxycarbonylamino group and an i-propoxycarbonylamino group;

an unsubstituted or substituted aminocarbonyl group such as an aminocarbonyl group, a dimethylaminocarbonyl group, a phenylaminocarbonyl group and an N-phenyl-N-methylaminocarbonyl group;

an imino $C_{1-6}$ alkyl group such as an iminomethyl group, a (1-imino)ethyl group and a (1-imino)-n-propyl group;

a substituted or unsubstituted N-hydroxyimino $C_{1-6}$ alkyl group such as an N-hydroxy-iminomethyl group, a (1-(N-hydroxy)-imino)ethyl group, a (1-(N-hydroxy)-imino)propyl group, an N-methoxy-iminomethyl group, and a (1-(N-methoxy)-imino)ethyl group;

an aminocarbonyloxy group;

a $C_{1-6}$ alkyl-substituted aminocarbonyloxy group such as an ethylaminocarbonyloxy group, and a dimethylaminocarbonyloxy group;

a mercapto group;

a $C_{1-6}$ alkylthio group such as a methylthio group, an ethylthio group, an n-propylthio group, an i-propylthio group, an n-butylthio group, an i-butylthio group, an s-butylthio group and a t-butylthio group;

a $C_{1-6}$ haloalkylthio group such as a trifluoromethylthio group and a 2,2,2-trifluoroethylthio group;

a $C_{6-10}$ arylthio group such as a phenylthio group and a naphthylthio group;

a 5- to 6-membered heteroarylthio group such as a thiazolylthio group and a pyridylthio group;

a $C_{1-6}$ alkylsulfinyl group such as a methylsulfinyl group, an ethylsulfinyl group and a t-butylsulfinyl group;

a $C_{1-6}$ haloalkylsulfinyl group such as a trifluoromethylsulfinyl group and a 2,2,2-trifluoroethylsulfinyl group;

a $C_{6-10}$ arylsulfinyl group such as a phenylsulfinyl group;

a 5- to 6-membered heteroarylsulfinyl group such as a thiazolylsulfinyl group and a pyridylsulfinyl group;

a $C_{1-6}$ alkylsulfonyl group such as a methylsulfonyl group, an ethylsulfonyl group and a t-butylsulfonyl group;

a $C_{1-6}$ haloalkylsulfonyl group such as a trifluoromethylsulfonyl group and a 2,2,2-trifluoroethylsulfonyl group;

a $C_{6-10}$ arylsulfonyl group such as a phenylsulfonyl group;

a 5- to 6-membered heteroarylsulfonyl group such as a thiazolylsulfonyl group and a pyridylsulfonyl group;

a $C_{1-6}$ alkylsulfonyloxy group such as a methylsulfonyloxy group, an ethylsulfonyloxy group and a t-butylsulfonyloxy group;

a $C_{1-6}$ haloalkylsulfonyloxy group such as a trifluoromethylsulfonyloxy group and a 2,2,2-trifluoroethylsulfonyloxy group;

a tri $C_{1-6}$ alkyl-substituted silyl group such as a trimethylsilyl group, a triethylsilyl group and a t-butyldimethylsilyl group;

a tri $C_{6-10}$ aryl-substituted silyl group such as a triphenylsilyl group;

a pentafluorosulfanyl group;

a cyano group; a nitro group.

Further, in these "substituents", any hydrogen atom in the substituent may be substituted with a group having a different structure. Examples of the "substituent" in this case include a $C_{1-6}$ alkyl group, a $C_{1-6}$ haloalkyl group, a $C_{1-6}$ alkoxy group, a $C_{1-6}$ haloalkoxy group, a halogeno group, a cyano group and a nitro group.

Further, the above-described "3- to 6-membered heterocyclyl group" includes 1 to 4 hetero atoms selected from the group consisting of a nitrogen atom, an oxygen atom and a sulfur atom as constituent atoms of the ring. The heterocyclyl group may be either monocyclic or polycyclic. As long as the polycyclic heterocyclyl group includes at least one heterocyclic ring, the remaining ring may be a saturated alicyclic ring, an unsaturated alicyclic ring or an aromatic ring. Examples of the "3- to 6-membered heterocyclyl group" include a 3- to 6-membered saturated heterocyclyl group, a 5- to 6-membered heteroaryl group, and a 5- to 6-membered partially unsaturated heterocyclyl group.

Examples of the 3- to 6-membered saturated heterocyclyl group include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, and a dioxanyl group.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group and a tetrazolyl group.

Examples of the 6-membered heteroaryl group include a pyridyl group, a pyrazinyl group, a pyrimidinyl group, a pyridazinyl group and a triazinyl group.

In the formula (ii), $Z^{q-}$ represents a counter ion, and q represents a valence of the counter ion and is 1 or 2. Specific examples of a monovalent anion $Z^-$ include $Cl^-$, $Br^-$, $I^-$, $NO_3^-$, $CH_3COO^-$, $CH_3SO_3^-$, $CF_3SO_3^-$ and $TolSO_3^-$. Specific examples of a bivalent anion $Z^{2-}$ include $SO_4^{2-}$ and the like. Tol is an abbreviation indicating an o-methylphenyl group, an m-methylphenyl group or a p-methylphenyl group.

[A]

In the formulas (I) and (II), A represents an oxygen atom or a sulfur atom.

In the present invention, A is preferably an oxygen atom.

[$X^1$, m]

In the formulas (I) and (II), $X^1$ represents a halogeno group, a substituted or unsubstituted $C_{1-6}$ alkyl group, a substituted or unsubstituted $C_{2-6}$ alkenyl group, a substituted or unsubstituted $C_{2-6}$ alkynyl group, a hydroxyl group, a substituted or unsubstituted $C_{1-6}$ alkoxy group, a substituted or unsubstituted $C_{2-6}$ alkenyloxy group, a substituted or unsubstituted $C_{2-6}$ alkynyloxy group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkylsulfonyloxy group, an amino group, a substituted or unsubstituted $C_{1-6}$ alkylamino group, a substituted or unsubstituted $C_{3-8}$ cycloalkyl group, a substituted or unsubstituted $C_{3-8}$ cycloalkyloxy group, a substituted or unsubstituted $C_{6-10}$ aryl group, a substituted or unsubstituted $C_{6-10}$ aryloxy group, a substituted or unsubstituted 5- to 6-membered heteroaryl group, a substituted or unsubstituted 5- to 6-membered heteroaryloxy group, a pentafluorosulfanyl group, a nitro group or a cyano group;

m represents the number of $X^t$ and is any integer of 0 to 5; and any two of $X^1$ may be bound together to form a bivalent hydrocarbon group.

As the "halogeno group" represented by $X^1$, a fluoro group, a chloro group, a bromo group, an iodo group and the like can be mentioned.

The "$C_{1-6}$ alkyl group" represented by $X^1$ may be linear or branched. Examples of the alkyl group include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group.

Examples of the "$C_{2-6}$ alkenyl group" represented by $X^1$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group and a 5-hexenyl group.

Examples of the "$C_{2-6}$ alkynyl group" represented by $X^1$ include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group and a 1,1-dimethyl-2-butynyl group.

Examples of the "$C_{1-6}$ alkoxy group" represented by $X^1$ include a methoxy group, an ethoxy group, an n-propoxy group, an n-butoxy group, an n-pentyloxy group, an n-hexyloxy group, an i-propoxy group, an i-butoxy group, an s-butoxy group, a t-butoxy group and an i-hexyloxy group.

Examples of the "$C_{2-6}$ alkenyloxy group" represented by $X^1$ include a vinyloxy group, an allyloxy group, a propenyloxy group and a butenyloxy group.

Examples of the "$C_{2-6}$ alkynyloxy group" represented by $X^1$ include an ethynyloxy group and a propargyloxy group.

Examples of the "$C_{1-6}$ alkylcarbonyl group" represented by $X^1$ include an acetyl group and a propionyl group.

Examples of the "$C_{1-6}$ alkoxycarbonyl group" represented by $X^1$ include a methoxycarbonyl group, an ethoxycarbonyl group, an n-propoxycarbonyl group, an i-propoxycarbonyl group and a t-butoxycarbonyl group.

Examples of the "$C_{1-6}$ alkylthio group" represented by $X^1$ include a methylthio group, an ethylthio group, an n-propylthio group, an n-butylthio group, an n-pentylthio group, an n-hexylthio group and an i-propylthio group.

Examples of the "$C_{1-6}$ alkylsulfinyl group" represented by $X^1$ include a methylsulfinyl group, an ethylsulfinyl group and a t-butylsulfinyl group.

Examples of the "$C_{1-6}$ alkylsulfonyl group" represented by $X^1$ include a methylsulfonyl group, an ethylsulfonyl group and a t-butylsulfonyl group.

Examples of the "$C_{1-6}$ alkylsulfonyloxy group" represented by $X^1$ include a methylsulfonyloxy group, an ethylsulfonyloxy group and a t-butylsulfonyloxy group.

Examples of the "$C_{1-6}$ alkylamino group" represented by $X^1$ include a mono $C_{1-6}$ alkylamino group such as a methylamino group and an ethylamino group; and a di $C_{1-6}$ alkylamino group such as a dimethylamino group and a diethylamino group.

Preferred examples of the substituents on the "$C_{1-6}$ alkyl group", "$C_{2-6}$ alkenyl group", "$C_{2-6}$ alkynyl group", "$C_{1-6}$ alkoxy group", "$C_{2-6}$ alkenyloxy group", "$C_{2-6}$ alkynyloxy group", "$C_{1-6}$ alkylcarbonyl group", "$C_{1-6}$ alkoxycarbonyl group", "$C_{1-6}$ alkylthio group", "$C_{1-6}$ alkylsulfinyl group", "$C_{1-6}$ alkylsulfonyl group", "$C_{1-6}$ alkylsulfonyloxy group" or "$C_{1-6}$ alkylamino group" represented by $X^1$ include a halogeno group such as a fluoro group, a chloro group, a bromo group and an iodo group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; a $C_{6-10}$ aryl group such as a phenyl group and a naphthyl group; and a cyano group.

Examples of the "$C_{3-8}$ cycloalkyl group" represented by $X^1$ include a cyclopropyl group, a cyclobutyl group, a cyclopentyl group, a cyclohexyl group and a cycloheptyl group.

Examples of the "$C_{3-8}$ cycloalkyloxy group" represented by $X^1$ include a cyclopropyloxy group, a cyclobutyloxy group, a cyclopentyloxy group, a cyclohexyloxy group and a cycloheptyloxy group.

Examples of the "$C_{6-10}$ aryl group" represented by $X^1$ include a phenyl group and a naphthyl group.

Examples of the "$C_{6-10}$ aryloxy group" represented by $X^1$ include a phenoxy group and a naphthoxy group.

The "5- to 6-membered heteroaryl group" represented by $X^1$ contains 1 to 4 hetero atoms selected from the group consisting of a nitrogen atom, an oxygen atom and a sulfur atom as constituent atoms of the ring. Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group and a tetrazolyl group, and examples of the 6-membered heteroaryl group include a pyridyl group, a pyrazinyl group, a pyrimidinyl group, a pyridazinyl group and a triazinyl group.

The "5- to 6-membered heteroaryloxy group" represented by $X^1$ is a structure in which a 5- or 6-membered heteroaryl group and an oxy group are bonded. Specific examples thereof include a thiazolyloxy group and a pyridyloxy group.

Preferred examples of the substituents on the "$C_{3-8}$ cycloalkyl group", "$C_{3-5}$ cycloalkyloxy group", "$C_{6-10}$ aryl group", "$C_{6-10}$ aryloxy group", "5- to 6-membered heteroaryl group" or "5- to 6-membered heteroaryloxy group" represented by $X^1$ include a halogeno group such as a fluoro group, a chloro group, a bromo group and an iodo group; a $C_{1-6}$ alkyl group such as a methyl group, an ethyl group, an n-propyl group, an i-propyl group, an n-butyl group, an s-butyl group, an i-butyl group, a t-butyl group, an n-pentyl group and an n-hexyl group; a $C_{1-6}$ haloalkyl group such as a chloromethyl group, a chloroethyl group, a trifluoromethyl group, a 1,2-dichloro-n-propyl group and a 1-fluoro-n-butyl group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; and a cyano group.

Examples of the "bivalent hydrocarbon group" formed by any two of $X^1$ together include a trimethylene group, a tetramethylene group, a vinylene group and a 1,3-butadiene-1,4-diyl group.

In the present invention, $X^1$ is preferably a halogeno group, a halogeno group-substituted or unsubstituted $C_{1-6}$ alkyl group, or a halogeno group-substituted or unsubstituted $C_{1-6}$ alkoxy group.

When $X^1$ is a halogeno group-substituted $C_{1-6}$ alkyl group, specific examples thereof include a $C_{1-6}$ haloalkyl group such as a difluoromethyl group, a trifluoromethyl group, a 2,2,2-trifluoroethyl group and a 2,2,2,1,1-pentafluoroethyl group.

When $X^1$ is a halogeno group-substituted $C_{1-6}$ alkoxy group, specific examples thereof include a $C_{1-6}$ haloalkoxy group such as a difluoromethoxy group, a trifluoromethoxy group, a 2,2-difluoroethoxy group, a 2,2,2-trifluoroethoxy group, a 2,2,1,1-tetrafluoroethoxy group and a 2,2,2,1,1-pentafluoroethoxy group.

[$Q^2$]

$Q^2$ represents a substituted or unsubstituted $C_{6-10}$ aryl group or a substituted or unsubstituted 5- to 6-membered heteroaryl group.

Examples of the "$C_{6-10}$ aryl group" represented by $Q^2$ include a phenyl group and a naphthyl group.

Examples of the "5- to 6-membered heteroaryl group" represented by $Q^2$ include a 5-membered heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group and a tetrazolyl group; and a 6-membered heteroaryl group such as a pyridyl group, a pyrazinyl group, a pyrimidinyl group, a pyridazinyl group, and a triazinyl group.

Examples of the substituent on the "$C_{6-10}$ aryl group" or "5- to 6-membered heteroaryl group" represented by $Q^2$ include a halogeno group, a substituted or unsubstituted $C_{1-6}$ alkyl group, a substituted or unsubstituted $C_{2-6}$ alkenyl group, a substituted or unsubstituted $C_{2-6}$ alkynyl group, a hydroxyl group, a substituted or unsubstituted $C_{1-6}$ alkoxy group, a substituted or unsubstituted $C_{2-6}$ alkenyloxy group, a substituted or unsubstituted $C_{2-6}$ alkynyloxy group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkylsulfonyloxy group, an amino group, a substituted or unsubstituted $C_{4-6}$ alkylamino group, a substituted or unsubstituted $C_{3-8}$ cycloalkyl group, a substituted or unsubstituted $C_{3-8}$ cycloalkyloxy group, a substituted or unsubstituted $C_{6-10}$ aryl group, a substituted or unsubstituted $C_{6-10}$ aryloxy group, a substituted or unsubstituted 5- to 6-membered heteroaryl group, a substituted or unsubstituted 5- to 6-membered heteroaryloxy group, a pentafluorosulfanyl group, a nitro group or a cyano group. Specific examples of these include the same ones as those exemplified for $X^1$. Further, the number of substituents on the "$C_{6-10}$ aryl group" or "5- to 6-membered heteroaryl group" represented by $Q^2$ can be 1 to 5.

In addition, any two substituents may form a bivalent organic group together.

In the present invention, as the substituent on the "$C_{6-10}$ aryl group" or "5- to 6-membered heteroaryl group" represented by $Q^2$, a halogeno group, a halogeno group-substituted or unsubstituted $C_{1-6}$ alkyl group, a halogeno group-substituted or unsubstituted $C_{2-6}$ alkynyl group, a hydroxyl group, a halogeno group-substituted or unsubstituted $C_{1-6}$ alkoxy group, a substituted or unsubstituted benzyl group, a halogeno group-substituted or unsubstituted $C_{1-6}$ alkoxycarbonyl group, a halogeno group-substituted or unsubstituted $C_{1-6}$ alkylthio group, a halogeno group-substituted or unsubstituted $C_{1-6}$ alkylsulfonyl group, a halogeno group-substituted or unsubstituted $C_{1-6}$ alkylsulfonyloxy group, a di $C_{1-6}$ alkylamino group, a halogeno group-substituted or unsubstituted $C_{3-8}$ cycloalkyl group, a halogeno group-substituted or unsubstituted $C_{3-8}$ cycloalkyloxy group, a substituted or unsubstituted phenyl group, a pentafluorosulfanyl group, or a cyano group is preferable.

When the substituent on the "$C_{6-10}$ aryl group" or "5- to 6-membered heteroaryl group" represented by $Q^2$ is a halogeno group-substituted $C_{1-6}$ alkyl group, specific examples thereof include a $C_{1-6}$ haloalkyl group such as a difluoromethyl group, a trifluoromethyl group, a 2,2,2-trifluoroethyl group, a 2,2,2,1,1-pentafluoroethyl group and a 3,3,3,2,2,1,1-heptafluoropropyl group.

When the substituent on the "$C_{6-10}$ aryl group" or "5- to 6-membered heteroaryl group" represented by $Q^2$ is a halogeno group-substituted $C_{1-6}$ alkoxy group, specific examples thereof include a $C_{1-6}$ haloalkoxy group such as a difluoromethoxy group, a trifluoromethoxy group, a 2,2-difluoroethoxy group, a 2,2,2-trifluoroethoxy group, a 2,2,1,1-tetrafluoroethoxy group, a 2,2,2,1,1-pentafluoroethoxy group, a 3,3,2,2-tetrafluoropropoxy group, a 3,3,3,2,2-pentafluoropropoxy group, a 3,3,3,2,1,1-hexafluoropropyloxy group and a 4,4,4,3,3,2,2-heptafluorobutoxy group.

When the substituent on the "$C_{6-10}$ aryl group" or "5- to 6-membered heteroaryl group" represented by $Q^2$ is a substituted benzyl group, the substituent on the benzyl group is preferably a halogeno group, a $C_{1-6}$ alkyl group, a $C_{1-6}$ haloalkyl group, a $C_{1-6}$ alkoxy group or a $C_{1-6}$ haloalkoxy group.

When the substituent on the "$C_{6-10}$ aryl group" or "5- to 6-membered heteroaryl group" represented by $Q^2$ is a substituted phenyl group, the substituent on the phenyl group is preferably a halogeno group, a $C_{1-6}$ alkyl group, a $C_{1-6}$ haloalkyl group, a $C_{1-6}$ alkoxy group or a $C_{1-6}$ haloalkoxy group.

Examples of the "bivalent organic group" formed by any two of the substituents together include a trimethylene group, a tetramethylene group, a vinylene group and a 1,3-butadiene-1,4-diyl group.

These bivalent organic groups may be substituted with a halogeno group, a $C_{1-6}$ alkyl group, a $C_{1-6}$ haloalkyl group or an oxo group (O=).

[Y]

Y represents a single bond or a substituted or unsubstituted $C_{2-6}$ alkenylene group.

Examples of the "$C_{2-6}$ alkenylene group" represented by Y include a vinylene group, a propenylene group and a butenylene group.

Examples of the substituent on the "$C_{2-6}$ alkenylene group" represented by Y include a halogeno group such as a fluoro group, a chloro group, a bromo group and an iodo group; a $C_{1-6}$ alkyl group such as a methyl group, an ethyl group, an n-propyl group, an i-propyl group, an n-butyl group, an s-butyl group, an i-butyl group and a t-butyl group; a $C_{1-6}$ haloalkyl group such as a chloromethyl group, a chloroethyl group, a trifluoromethyl group, a 1,2-dichloro-n-propyl group and a 1-fluoro-n-butyl group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; a $C_{1-6}$ alkylthio group such as a methylthio group, an ethylthio group, an n-propylthio group, an i-propylthio group, an n-butylthio group, an i-butylthio group, an s-butylthio group and a t-butylthio group; a $C_{1-6}$ alkylsulfinyl group such as a methylsulfinyl group, an ethylsulfinyl group and a t-butylsulfinyl group; and a $C_{1-6}$ alkylsulfonyl group such as a methylsulfonyl group, an ethylsulfonyl group and a t-butylsulfonyl group.

In the present invention, the substituent on the "$C_{2-6}$ alkenylene group" represented by Y is preferably a halogeno group, a halogeno group-substituted or unsubstituted $C_{1-6}$ alkyl group, or a halogeno group-substituted or unsubstituted $C_{1-6}$ alkoxy group.

[$Q^1$]

$Q^1$ represents a substituted or unsubstituted $C_{6-10}$ arylene group or a substituted or unsubstituted 6- to 10-membered heteroarylene group.

Examples of the "$C_{6-10}$ arylene group" represented by $Q^1$ include a phenylene group such as a 1,2-phenylene group, a 1,3-phenylene group and a 1,4-phenylene group, and a naphthylene group such as a 2,6-naphthylene group.

Examples of the "6- to 10-membered heteroarylene group" represented by $Q^1$ include a 6-membered heteroarylene group such as a pyridylene group, a pyrazinylene group, a pyrimidinylene group, a pyridazinylene group and a triazinylene group; an indolediyl group such as a 1H-indole-2,6-diyl group; a benzofurandiyl group such as a benzo[b]furan-2,6-diyl group; a benzothiophenediyl group such as a benzo[b]thiophene-2,6-diyl group; a benzoxazolediyl group such as a benzoxazole-2,5-diyl group and a benzoxazole-2,6-diyl group; a 9-membered heteroarylene group such as a benzothiazolediyl group such as a benzothiazole-2,5-diyl group and a benzothiazole-2,6-diyl group; and a 10-membered heteroarylene group such as a quinolinediyl group, an isoquinolinediyl group and a quinoxalinediyl group.

Examples of the substituent $X^2$ on the "$C_{6-10}$ arylene group" or "6- to 10-membered heteroarylene group" represented by $Q^1$ include a halogeno group such as a fluoro group, a chloro group, a bromo group, and an iodo group; a $C_{1-6}$ alkyl group such as a methyl group, an ethyl group, an n-propyl group, an i-propyl group, an n-butyl group, an s-butyl group, an i-butyl group and a t-butyl group; a $C_{1-6}$ haloalkyl group such as a chloromethyl group, a chloroethyl group, a trifluoromethyl group, a 1,2-dichloro-n-propyl group and a 1-fluoro-n-butyl group; a hydroxyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; a $C_{1-6}$ alkylthio group such as a methylthio group, an ethylthio group, an n-propylthio group, an i-propylthio group, an n-butylthio group, an i-butylthio group, an s-butylthio group and a t-butylthio group; a $C_{1-6}$ alkylsulfinyl group such as a methylsulfinyl group, an ethylsulfinyl group and a t-butylsulfinyl group; a $C_{1-6}$ alkylsulfonyl group such as a methylsulfonyl group, an ethylsulfonyl group and a t-butylsulfonyl group; and a nitro group. The number n of the substituents $X^2$ on the "$C_{6-10}$ arylene group" or "6- to 10-membered heteroarylene group" represented by $Q^1$ can be 1 to 2.

Among them, $Q^1$ is preferably a substituted or unsubstituted 1,4-phenylene group, a substituted or unsubstituted 1H-indolediyl group, a substituted or unsubstituted 1-benzofurandiyl group, a substituted or unsubstituted 1-benzothiophenediyl group, a substituted or unsubstituted 1,3-benzoxazolediyl group, a substituted or unsubstituted 1,3-benzothiazolediyl group and a 1H-benzimidazolediyl group.

In the present invention, the substituent $X^2$ is preferably a halogeno group, a halogeno group-substituted or unsubstituted $C_{1-6}$ alkyl group, a halogeno-substituted or unsubstituted $C_{1-6}$ alkoxy group, or a nitro group.

Specific examples of preferred pyridinium salts of the present invention include compounds represented by formula (I-a) or formula (II-a); compounds represented by formula (I-b) or formula (II-b); and compounds represented by formula (I-c) or formula (II-c).

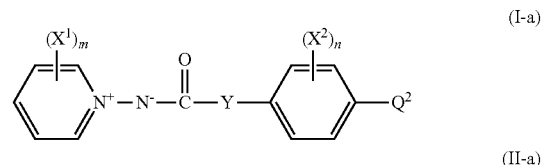
(I-a)

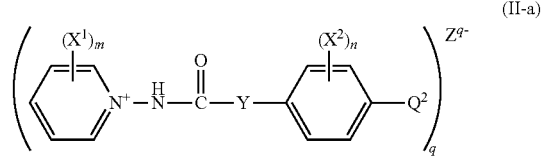
(II-a)

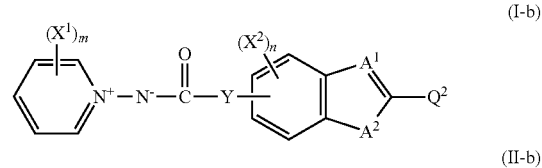
(I-b)

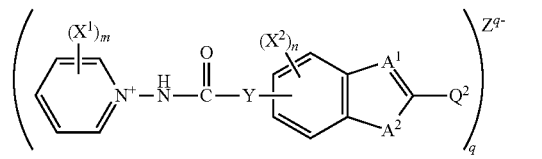
(II-b)

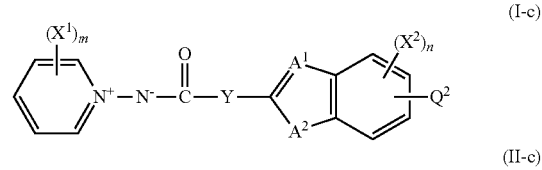
(I-c)

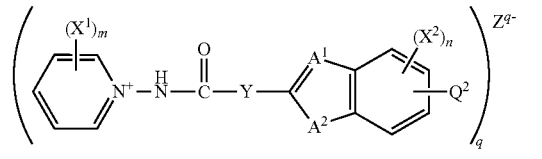
(II-c)

$X^1$, m, Y and $Q^2$ in the formulas (I-a), (II-a), (I-b), (II-b), (I-c) and (II-c) are the same as those defined in formula (I) or formula (II).

Z and q in the formulas (II-a), (II-b) and (II-c) are the same as those defined in formula (I) or formula (II).

$X^2$ and n in the formulas (I-a), (II-a), (I-b), (II-b), (I-c) and (II-c) are the same as the substituent $X^2$ on the "$C_{6-10}$ arylene group" or "6- to 10-membered heteroarylene group" represented by $Q^1$ and the number n thereof.

In the formulas (I-b), (II-b), (I-c) and (II-c), $A^1$ represents a nitrogen atom, a group represented by CH or a group represented by $CX^2$, and $A^2$ represents an oxygen atom, a sulfur atom, a group represented by NH, or a group represented by $NX^2$. $X^2$ is the same as the substituent $X^2$ on the "$C_{6-10}$ arylene group" or "6- to 10-membered heteroarylene group" represented by Q'.

The pyridinium salt of the present invention is not particularly limited by its production method. For example, the pyridinium salt of the present invention (hereinafter sometimes referred to as the "compound of the present invention") can be obtained using a known reaction described in Examples and the like.

The compound of the present invention is excellent in the effect of controlling harmful organisms such as various agricultural pests affecting the growth of plants, and mites and ticks.

In addition, the compound of the present invention is a highly safe material because it has less phytotoxicity to crops and has low toxicity to fish and warm-blooded animals. Therefore, it is useful as an active ingredient of insecticides or acaricides.

Furthermore, in recent years, resistance to various existing drugs has developed in a number of insect pests such as diamondback moths, planthoppers, leafhoppers and aphids, causing problems of insufficient efficacy of these drugs, and drugs that are effective even against resistant strains of insect pests have been desired. The compound of the present invention exhibits an excellent controlling effect not only on susceptible strains but also on various resistant strains of insect pests and acaricide-resistant strains of mites and ticks.

The compound of the present invention is excellent in the effect of controlling ectoparasites and endoparasites which harm humans and animals. In addition, it is a highly safe material because of its low toxicity to fish and warm-blooded animals. Therefore, it is useful as an active ingredient of an agent for controlling ectoparasites and endoparasites.

In addition, the compound of the present invention shows efficacy in all developmental stages of organisms to be controlled, and shows excellent control effect, for example, on eggs, nymphs, larvae, pupae and adults of mites and ticks, insects and the like.

[Pest Control Agent, Insecticidal or Acaricidal Agent]

The pest control agent or the insecticidal or acaricidal agent of the present invention contains at least one selected from the pyridinium salts of the present invention as an active ingredient. The amount of the compound of the present invention contained in the pest control agent or the insecticidal or acaricidal agent of the present invention is not particularly limited as long as it shows the effect of controlling harmful organisms, agricultural pests or mites and ticks.

The pest control agent or the insecticidal or acaricidal agent of the present invention is preferably used for grains; vegetables; root vegetables; potatoes; flowers and ornamental plants; fruit trees; foliage plants and trees of tea, coffee, cacao and the like; pasture grasses; turf grasses; and plants such as cotton.

In application to plants, the pest control agent or the insecticidal or acaricidal agent of the present invention may be used to any portions of leaves, stems, stalks, flowers, buds, fruits, seeds, sprouts, roots, tubers, tuberous roots, shoots, cuttings and the like.

Further, the pest control agent or the insecticidal or acaricidal agent of the present invention is not particularly limited depending on the species of the plant to be applied. Examples of the plant species include an original species, a variant species, an improved variety, a cultivar, a mutant, a hybrid and a genetically modified organism (GMO).

The pest control agent of the present invention can be used for seed treatment, foliage application, soil application, water surface application and the like, in order to control various agricultural pests and mites and ticks.

Specific examples of the various agricultural pests and mites that can be controlled by the pest control agent of the present invention are listed below.

(1) Lepidoptera Butterflies and Moths (a) Arctiidae moths, for example, *Hyphantria cunea* and *Lemyra imparilis*;

(b) Bucculatricidae moths, for example, *Bucculatrix pyrivorella*;

(c) Carposinidae, for example, *Carposina sasakii*;

(d) Crambidae moths, for example, *Diaphania indica* and *Diaphania nitidalis* of *Diaphania* spp.; *Ostrinia furnacalis*, *Ostrinia nubilalis* and *Ostrinia scapulalis* of *Ostrinia* spp.; and others such as *Chilo suppressalis, Cnaphalocrocis medinalis, Conogethes punctiferalis, Diatraea grandiosella, Glyphodes pyloalis, Hellula undalis* and *Parapediasia teterrella*;

(e) Gelechiidae moths, for example, *Helcystogramma triannulella, Pectinophora gossypiella, Phthorimaea operculella* and *Sitotroga cerealella*;

(f) Geometridae moths, for example, *Ascotis selenaria*;

(g) Gracillariidae moths, for example, *Caloptilia theivora, Phyllocnistis citrella* and *Phyllonorycter ringoniella*;

(h) Hesperiidae butterflies, for example, *Parnara guttata*;

(i) Lasiocampidae moths, for example, *Malacosoma neustria*;

(j) Lymantriidae moths, for example, *Lymantria dispar* and *Lymantria monacha* of *Lymantria* spp.; and others such as *Euproctis pseudoconspersa* and *Orgyia thyellina*;

(k) Lyonetiidae moths, for example, *Lyonetia clerkella* and *Lyonetia prunifoliella malinella* of *Lyonetia* spp.;

(l) Noctuidae moths, for example, *Spodoptera depravata, Spodoptera eridania, Spodoptera exigua, Spodoptera frugiperda, Spodoptera littoralis* and *Spodoptera litura* of *Spodoptera* spp.; *Autographa gamma* and *Autographa nigrisigna* of *Autographa* spp.; *Agrotis ipsilon* and *Agrotis segetum* of *Agrotis* spp.; *Helicoverpa armigera, Helicoverpa assulta* and *Helicoverpa zea* of *Helicoverpa* spp.; *Heliothis armigera* and *Heliothis virescens* of *Heliothis* spp.; and others such as *Aedia leucomelas, Ctenoplusia agnata, Eudocima tyrannus, Mamestra brassicae, Mythimna separata, Naranga aenescens, Panolis japonica, Peridroma saucia, Pseudoplusia includens* and *Trichoplusia ni*;

(m) Nolidae moths, for example, *Earias insulana*;

(n) Pieridae butterflies, for example, *Pieris brassicae* and *Pieris rapae crucivora* of *Pieris* spp.;

(o) Plutellidae moths, for example, *Acrolepiopsis sapporensis* and *Acrolepiopsis suzukiella* of *Acrolepiopsis* spp.; and others such as *Plutella xylostella*;

(p) Pyralidae moths, for example, *Cadra cautella, Elasmopalpus lignosellus, Etiella zinckenella* and *Galleria mellonella*;

(q) Sphingidae moths, for example, *Manduca quinquemaculata* and *Manduca sexta* of *Manduca* spp.;

(r) Stathmopodidae moths, for example, *Stathmopoda masinissa*;
(s) Tineidae moths, for example, *Tinea translucens*;
(t) Tortricidae moths, for example, *Adoxophyes honmai* and *Adoxophyes orana* of *Adoxophyes* spp.; *Archips breviplicanus* and *Archips fuscocupreanus* of *Archips* spp.; and others such as *Choristoneura fumiferana*, *Cydia pomonella*, *Eupoecilia ambiguella*, *Grapholitha molesta*, *Homona magnanima*, *Leguminivora glycinivorella*, *Lobesia botrana*, *Matsumuraeses phaseoli*, *Pandemis heparana* and *Sparganothis pilleriana*; and
(u) Yponomeutidae moths, for example, *Argyresthia conjugella*.
(2) Thysanoptera Insect Pests
(a) Phlaeothripidae, for example, *Ponticulothrips diospyrosi*; and
(b) Thripidae, for example, *Frankliniella intonsa* and *Frankliniella occidentalis* of *Frankliniella* spp.; *Thrips palmi* and *Thrips tabaci* of *Thrips* spp.; and others such as *Heliothrips haemorrhoidalis* and *Scirtothrips dorsalis*.
(3) Hemiptera Insect Pests
(A) Archaeorrhyncha
(a) Delphacidae, for example, *Laodelphax striatella*, *Nilaparvata lugens*, *Perkinsiella saccharicida* and *Sogatella furcifera*.
(B) Clypeorrhyncha
(a) Cicadellidae, for example, *Empoasca fabae*, *Empoasca nipponica*, *Empoasca onukii* and *Empoasca sakaii* of *Empoasca* spp.; and others such as *Arboridia apicalis*, *Balclutha saltuella*, *Epiacanthus stramineus*, *Macrosteles striifrons* and *Nephotettix cinctinceps*.
(C) Heteroptera
(a) Alydidae, for example, *Riptortus clavatus*;
(b) Coreidae, for example, *Cletus punctiger* and *Leptocorisa chinensis*;
(c) Lygaeidae, for example, *Blissus leucopterus*, *Cavelerius saccharivorus* and *Togo hemipterus*;
(d) Miridae, for example, *Halticus insularis*, *Lygus lineolaris*, *Psuedatomoscelis seriatus*, *Stenodema sibiricum*, *Stenotus rubrovittatus* and *Trigonotylus caelestialium*;
(e) Pentatomidae, for example, *Nezara antennata* and *Nezara viridula* of *Nezara* spp.; *Eysarcoris aeneus*, *Eysarcoris lewisi* and *Eysarcoris ventralis* of *Eysarcoris* spp.; and others such as *Dolycoris baccarum*, *Eurydema rugosum*, *Glaucias subpunctatus*, *Halyomorpha halys*, *Piezodorus hybneri*, *Plautia crossota* and *Scotinophora lurida*;
(f) Pyrrhocoridae, for example, *Dysdercus cingulatus*;
(g) Rhopalidae, for example, *Rhopalus msculatus*;
(h) Scutelleridae, for example, *Eurygaster integriceps*; and
(i) Tingidae, for example, *Stephanitis nashi*.
(D) Sternorrhyncha
(a) Adelgidae, for example, *Adelges laricis*;
(b) Aleyrodidae, for example, *Bemisia argentifolii* and *Bemisia tabaci* of *Bemisia* spp.; and others such as *Aleurocanthus spiniferus*, *Dialeurodes citri* and *Trialeurodes vaporariorum*;
(c) Aphididae, for example, *Aphis craccivora*, *Aphis fabae*, *Aphis forbesi*, *Aphis gossypii*, *Aphis pomi*, *Aphis sambuci* and *Aphis spiraecola* of *Aphis* spp.; *Rhopalosiphum maidis* and *Rhopalosiphum padi* of *Rhopalosiphum* spp.; *Dysaphis plantaginea* and *Dysaphis radicola* of *Dysaphis* spp.; *Macrosiphum avenae* and *Macrosiphum euphorbiae* of *Macrosiphum* spp.; *Myzus cerasi*, *Myzus persicae* and *Myzus varians* of *Myzus* spp.; and others such as *Acyrthosiphon pisum*, *Aulacorthum solani*, *Brachycaudus helichrysi*, *Brevicoryne brassicae*, *Chaetosiphon fragaefolii*, *Hyalopterus pruni*, *Hyperomyzus lactucae*, *Lipaphis erysimi*, *Megoura viciae*, *Metopolophium dirhodum*, *Nasonovia ribis-nigri*, *Phorodon humuli*, *Schizaphis graminum*, *Sitobion avenae* and *Toxoptera aurantii*;
(d) Coccidae, for example, *Ceroplastes ceriferus* and *Ceroplastes rubens* of *Ceroplastes* spp.;
(e) Diaspididae, for example, *Pseudaulacaspis pentagona* and *Pseudaulacaspis prunicola* of *Pseudaulacaspis* spp.; *Unaspis euonymi* and *Unaspis yanonensis* of *Unaspis* spp.; and others such as *Aonidiella aurantii*, *Comstockaspis perniciosa*, *Fiorinia theae* and *Pseudaonidia paeoniae*;
(f) Margarodidae, for example, *Drosicha corpulenta* and *Icerya purchasi*;
(g) Phylloxeridae, for example, *Viteus vitifolii*;
(h) Pseudococcidae, for example, *Planococcus citri* and *Planococcus kuraunhiae* of *Planococcus* spp.; and others such as *Phenacoccus solani* and *Pseudococcus comstocki*; and
(i) Psyllidae, for example, *Psylla mali* and *Psylla pyrisuga* of *Psylla* spp.; and others such as *Diaphorina citri*.
(4) Polyphaga Insect Pests
(a) Anobiidae, for example, *Lasioderma serricorne*;
(b) Attelabidae, for example, *Byctiscus betulae* and *Rhynchites heros*;
(c) Bostrichidae, for example, *Lyctus brunneus*;
(d) Brentidae, for example, *Cylas formicarius*;
(e) Buprestidae, for example, *Agrilus sinuatus*;
(f) Cerambycidae, for example, *Anoplophora malasiaca*, *Monochamus alternatus*, *Psacothea hilaris* and *Xylotrechus pyrrhoderus*;
(g) Chrysomelidae, for example, *Bruchus pisorum* and *Bruchus rufimanus* of *Bruchus* spp.; *Diabrotica barberi*, *Diabrotica undecimpunctata* and *Diabrotica virgifera* of *Diabrotica* spp.; *Phyllotreta nemorum* and *Phyllotreta striolata* of *Phyllotreta* spp.; and others such as *Aulacophora femoralis*, *Callosobruchus chinensis*, *Cassida nebulosa*, *Chaetocnema concinna*, *Leptinotarsa decemlineata*, *Oulema oryzae* and *Psylliodes angusticollis*;
(h) Coccinellidae, for example, *Epilachna varivestis* and *Epilachna vigintioctopunctata* of *Epilachna* spp.;
(i) Curculionidae, for example, *Anthonomus grandis* and *Anthonomus pomorum* of *Anthonomus* spp.; *Sitophilus granarius* of *Sitophilus zeamais* of *Sitophilus* spp.; and others such as *Echinocnemus squameus*, *Euscepes postfasciatus*, *Hylobius abietis*, *Hypera postica*, *Lissohoptrus oryzophilus*, *Otiorhynchus sulcatus*, *Sitona lineatus* and *Sphenophorus venatus*;
(j) Elateridae, for example, *Melanotus fortnumi* and *Melanotus tamsuyensis* of *Melanotus* spp.;
(k) Nitidulidae, for example, *Epuraea domina*;
(l) Scarabaeidae, for example, *Anomala cuprea* and *Anomala rufocuprea* of *Anomala* spp.; and others such as *Cetonia aurata*, *Gametis jucunda*, *Heptophylla picea*, *Melolontha melolontha* and *Popillia japonica*;
(m) Scolytidae, for example, *Ips typographus*;
(n) Staphylinidae, for example, *Paederus fuscipes*;
(o) Tenebrionidae, for example, *Tenebrio molitor* and *Tribolium castaneum*; and
(p) Trogossitidae, for example, *Tenebroides mauritanicus*.
(5) Diptera Insect Pests
(A) Brachycera
(a) Agromyzidae, for example, *Liriomyza bryoniae*, *Liriomyza chinensis*, *Liriomyza sativae* and *Liriomyza trifolii* of *Liriomyza* spp.; and others such as *Chromatomyia horticola* and *Agromyza oryzae*;
(b) Anthomyiidae, for example, *Delia platura* and *Delia radicum* of *Delia* spp.; and others such as *Pegomya cunicularia*;

(c) Drosophilidae, for example, *Drosophila melanogaster* and *Drosophila suzukii* of *Drosophila* spp.;
(d) Ephydridae, for example, *Hydrellia griseola;*
(e) Psilidae, for example, *Psila rosae;* and
(f) Tephritidae, for example, *Bactrocera cucurbitae* and *Bactrocera dorsalis* of *Bactrocera* spp.; *Rhagoletis cerasi* and *Rhagoletis pomonella* of *Rhagoletis* spp.; and others such as Ceratitis capitata and *Dacus oleae.*
(B) Nematocera
(a) Cecidomyiidae, for example, *Asphondylia yushimai, Contarinia sorghicola, Mayetiola destructor* and *Sitodiplosis mosellana.*
(6) Orthoptera Insect Pests
(a) Acrididae, for example, *Schistocerca americana* and *Schistocerca gregaria* of *Schistocerca* spp.; and others such as *Chortoicetes terminifera, Dociostaurus maroccanus, Locusta migratoria, Locustana pardalina, Nomadacris septemfasciata* and *Oxya yezoensis;*
(b) Gryllidae, for example, *Acheta domestica* and *Teleogryllus emma;*
(c) Gryllotalpidae, for example, *Gryllotalpa orientalis;* and
(d) Tettigoniidae, for example, *Tachycines asynamorus.*
(7) Acari
(A) Acaridida of Astigmata
(a) Acaridae mites, for example, *Rhizoglyphus echinopus* and *Rhizoglyphus robini* of *Rhizoglyphus* spp.; *Tyrophagus neiswanderi, Tyrophagus perniciosus, Tyrophagus putrescentiae* and *Tyrophagus similis* of *Tyrophagus* spp.; and others such as *Acarus siro, Aleuroglyphus ovatus* and *Mycetoglyphus fungivorus;*
(B) Actinedida of Prostigmata
(a) Tetranychidae mites, for example, *Bryobia praetiosa* and *Bryobia rubrioculus* of *Bryobia* spp.; *Eotetranychus asiaticus, Eotetranychus boreus, Eotetranychus celtis, Eotetranychus geniculatus, Eotetranychus kankitus, Eotetranychus pruni, Eotetranychus shii, Eotetranychus smithi, Eotetranychus suginamensis* and *Eotetranychus uncatus* of *Eotetranychus* spp.; *Oligonychus hondoensis, Oligonychus ilicis, Oligonychus karamatus, Oligonychus mangiferus, Oligonychus orthius, Oligonychus perseae, Oligonychus pustulosus, Oligonychus shinkajii* and *Oligonychus ununguis* of *Oligonychus* spp.; *Panonychus citri, Panonychus mors* and *Panonychus ulmi* of *Panonychus* spp.; *Tetranychus cinnabarinus, Tetranychus evansi, Tetranychus kanzawai, Tetranychus ludeni, Tetranychus quercivorus, Tetranychus phaselus, Tetranychus urticae* and *Tetranychus viennensis* of *Tetranychus* spp.; *Aponychus corpuzae* and *Aponychus firmianae* of *Aponychus* spp.; *Sasanychus akitanus* and *Sasanychus pusillus* of *Sasanychus* spp.; *Shizotetranychus celarius, Shizotetranychus longus, Shizotetranychus miscanthi, Shizotetranychus recki* and *Shizotetranychus schizopus* of *Shizotetranychus* spp.; and others such as *Tetranychina harti, Tuckerella pavoniformis* and *Yezonychus sapporensis;*
(b) Tenuipalpidae mites, for example, *Brevipalpus lewisi, Brevipalpus obovatus, Brevipalpus phoenicis, Brevipalpus russulus* and *Brevipalpus californicus* of *Brevipalpus* spp.; *Tenuipalpus pacificus* and *Tenuipalpus zhizhilashviliae* of *Tenuipalpus* spp.; and others such as Dolichotetranychus floridanus;
(c) Eriophyidae mites, for example, *Aceria diospyri, Aceria ficus, Aceria japonica, Aceria kuko, Aceria paradianthi, Aceria tiyingi, Aceria tulipae* and *Aceria zoysiea* of *Aceria* spp.; *Eriophyes chibaensis* and *Eriophyes emarginatae* of *Eriophyes* spp.; *Aculops lycopersici* and *Aculops pelekassi* of *Aculops* spp.; *Aculus fockeui* and *Aculus schlechtendali* of *Aculus* spp.; and others such as Acaphylla theavagrans, Calacarus carinatus, Colomerus vitis, Calepitrimerus vitis, Epitrimerus pyri, Paraphytoptus kikus, Paracalacarus podocarpi and Phyllocotruta citri;
(d) Transonemidae mites, for example, *Tarsonemus bilobatus* and *Tarsonemus waitei* of *Tarsonemus* spp.; and others such as *Phytonemus pallidus* and *Polyphagotarsonemus latus;* and
(e) Penthaleidae mites, for example, *Penthaleus erythrocephalus* and *Penthaleus major* of *Penthaleus* spp.

The pest control agent of the present invention may be mixed with or used in combination with other active ingredients such as fungicides, insecticidal and acaricidal agents, nematicides and soil pesticides; plant regulators, synergists, fertilizers, soil conditioners, animal feeds and the like.

A combination of the compound of the present invention and other active ingredients can be expected to have a synergistic effect on insecticidal, acaricidal and nematicidal activities. The synergistic effect can be confirmed by the Colby's formula (Colby, S. R.; Calculating Synergistic and Antagonistic Responses of Herbicide Combinations; Weeds 15, 20-22, 1967) according to a conventional method.

Specific examples of insecticides, miticides, nematicides, soil pesticides, and parasiticides and the like that can be mixed or used in combination with the pest control agent of the present invention are listed below.
(1) Acetylcholinesterase inhibitors:
(a) Carbamate-based: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylycarb, fenothiocarb, MIPC, MPMC, MTMC, aldoxycarb, allyxycarb, aminocarb, bufencarb, cloethocarb, metam-sodium, and promecarb; and
(b) Organophosphorus-based: acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinfos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridafenthion, quinalphos, sulfotep, tebupirimfos, temephos, terbufos, tetrachlorvinphos, thiometon, triazophos, trichlorfon, vamidothion, bromophos-ethyl, BRP, carbophenothion, cyanofenphos, demeton-S-methyl sulfone, dialifos, dichlofenthion, dioxabenzofos, etrimfos, fensulfothion, flupyrazofos, fonofos, formothion, fosmethilan, isazophos, iodofenphos, methacrifos, pirimiphos-ethyl, phosphocarb, propaphos, prothoate, and sulprofos.
(2) GABA receptor chloride ion channel antagonists: acetoprole, chlordane, endosulfan, ethiprole, fipronil, pyrafluprole, pyriprole, camphechlor, heptachlor, and dienochlor.
(3) Sodium channel modulators: acrinathrin, d-cis/trans-allethrin, d-trans-allethrin, bifenthrin, bioallethrin, bioallethrin S-cyclopentyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], delta-methrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrum, resmethrin, silafluofen, tefluthrin, tetramethrin [(1R)-isomer], tralomethrin, transfluthrin, allethrin, pyrethrin, pyrethrin I, pyrethrin II, profluthrin, dimefluthrin, bioethanomethrin, biopermethrin, transpermethirn, fenfluthrin, fenpyrithrin, flubrocythrinate, flufenoprox, metofluthrin, protrifenbute, pyresmethrin, and terallethrin.

(4) Nicotinic acetylcholine receptor agonists: acetamiprid, clothianidin, dinotefuran, imidacloprid, nitenpyram, nithiazine, thiacloprid, thiamethoxam, sulfoxaflor, nicotine, flupyradifurone, and flupyrimin (5) Nicotinic acetylcholine receptor allosteric modulators: spinetoram and spinosad.

(6) Chloride channel activators: abamectin, emamectin-benzoate, lepimectin, milbemectin, ivermectin, seramectin, doramectin, eprinomectin, moxidectin, milbemycin, milbemycin oxime, and nemadectin.

(7) Juvenile hormone-like substances: hydroprene, kinoprene, methoprene, fenoxycarb, pyriproxyfen, diofenolan, epofenonane, and triprene.

(8) Other nonspecific inhibitors: methyl bromide, chloropicrin, sulfuryl fluoride, borax, and tartar emetic.

(9) Homoptera selective feeding inhibitors: flonicamid, pymetrozine, and pyrifluquinazon.

(10) Mite growth inhibitors: clofentezine, diflovidazin, hexythiazox, and etoxazole.

(11) Microorganism-derived insect midgut inner membrane disrupting agents: *Bacillus thuringiensis* subsp. *israelensis*, *Bacillus sphaericus*, *Bacillus thuringiensis* subsp. *aizawai*, *Bacillus thuringiensis* subsp. *kurstaki*, *Bacillus thuringiensis* subsp. *tenebrionis*, Bt crop protein: Cry1Ab, Cry1Ac, Cry1 Fa, Cry1A.105, Cry2Ab, Vip3A, mCry3A, Cry3Ab, Cry3Bb, Cry34Ab1/Cry35Ab1.

(12) Mitochondria ATP biosynthesis enzyme inhibitors: diafenthiuron, azocyclotin, cyhexatin, fenbutatin oxide, propargite, and tetradifon.

(13) Oxidative phosphorylation uncoupling agents: chlorfenapyr, sulfluramid, DNOC, binapacryl, dinobuton, and dinocap.

(14) Nicotinic acetylcholine receptor channel blockers: bensultap, cartap hydrochloride, nereistoxin, thiosultap-sodium, and thiocyclarm.

(15) Chitin synthesis inhibitors: bistrifluron, chlorfluazuron, diflubenzuron, flucycloxuron, flufenoxuron, hexaflumuron, lufenuron, novaluron, novifumuron, teflubenzuron, triflumuron, buprofezin, and fluazuron.

(16) Diptera molting disturbing agent: cyromazine.

(17) Molting hormone receptor agonists: chromafenozide, halofenozide, methoxyfenozide, and tebufenozide.

(18) Octopamine receptor agonists: amitraz, demiditraz, and chlordimeform

(19) Mitochondria electron transfer chain complex III inhibitors: acequinocyl, fluacrypyrim, hydramethylnon, and bifenazate.

(20) Mitochondria electron transfer chain complex I inhibitors: fenazaquin, fenproximate, pyrimidifen, pyridaben, tebufenpyrad, tolfenpyrad, and rotenone.

(21) Voltage-dependent sodium channel blockers: indoxacarb and metaflumizone.

(22) Acetyl CoA carboxylase inhibitors: spirodiclofen, spiromesifen, spirotetramat, and spiropidion.

(23) Mitochondria electron transfer chain complex IV inhibitors: aluminium phosphide, calcium phosphide, phosphine, zinc phosphide, and cyanide.

(24) Mitochondria electron transfer chain complex II inhibitors: cyenopyrafen, cyflumetofen, and pyflubumide.

(25) Ryanodine receptor modulators: chlorantraniliprole, cyantraniliprole, flubendiamide, cyclaniliprole, and tetraniliprole.

(26) Mixed function oxidase inhibitor compound: piperonyl butoxide.

(27) Latrophilin receptor agonists: depsipeptide, cyclodepsipeptide, 24-membered cyclodepsipeptide, emodepside.

(28) Others (for which the mode of action is unknown): acynonapyr, azadirachtin, benzoximate, bromopropylate, quinomethionate, cryolite, dicofol, pyridalyl; benclothiaz, sulfur, amidoflumet, 1,3-dichloropropene, DCIP, phenisobromolate, benzomate, metaldehyde, chlorobenzilate, chlothiazoben, dicyclanil, fenoxacrim, fentrifanil, flubenzimine, fluphenazine, gossyplure, japonilure, metoxadiazone, oil, sodium oleate, tetrasul, triarathene, afidopyropen, flometoquin, flufiprole, fluensulfone, meperfluthrin, tetramethylfluthrin, tralopyril, methylneodecanamide, fluralaner, afoxolaner, fluxametamide, 5-[5-(3,5-dichlorophenyl)-5-trifluoromethyl-4,5-dihydroisoxazol-3-yl]-2-(1H-1,2,4-triazol-1-yl)benzonitrile (CAS:943137-49-3), broflanilide, triflumezopyrim, dicloromezotiaz, oxazosulfyl, other metadiamides, and tyclopyrazoflor.

(29) Parasiticides:

(a) Benzimidazole-based: fenbendazole, albendazole, triclabendazole, oxibendazole, mebendazole, oxfendazole, parbendazole, flubendazole, febantel, netobimin, thiophanate, thiabendazole, and cambendazole;

(b) Salicylanilide-based: closantel, oxyclozanide, rafoxanide, and niclosamide;

(c) Substituted phenol-based: nitroxinil, nitroscanate;

(d) Pyrimidine-based: pyrantel and morantel;

(e) Imidazothiazole-based: levamisole and tetramisole;

(f) Tetrahydropyrimidine-based: praziquantel and epsiprantel; and (g) Other parasiticides: cyclodiene, ryania, clorsulon, metronidazole, demiditraz, piperazine, diethylcarbamazine, dichlorophen, monepantel, tribendimidine, amidantel, thiacetarsamide, melarsomine, and arsenamide.

Specific examples of fungicides that can be mixed or used in combination with the pest control agent of the present invention are listed below.

(1) Nucleic acid biosynthesis inhibitors:

(a) RNA polymerase I inhibitors: benalaxyl, benalaxyl-M, furalaxyl, metalaxyl, metalaxyl-M, oxadixyl, clozylacon, and ofurace;

(b) Adenosine deaminase inhibitors: bupirimate, dimethirimol, and ethirimol;

(c) DNA/RNA synthesis inhibitors: hymexazol and octhilinone; and (d) DNA topoisomerase 11 inhibitor: oxolinic acid.

(2) Mitotic inhibitors and cell division inhibitors:

(a) β-tubulin polymerization inhibitors: benomyl, carbendazim, chlorfenazole, fuberidazole, thiabendazole, thiophanate, thiophanate-methyl, diethofencarb, zoxamide, and ethaboxam;

(b) Cell division inhibitor: pencycuron; and (c) Delocalization inhibitor of spectrin-like proteins: fluopicolide.

(3) Respiration inhibitors:

(a) Complex I NADH oxidoreductase inhibitors: diflumetorim and tolfenpyrad;

(b) Complex II succinic acid dehydrogenase inhibitors: benodanil, flutolanil, mepronil, isofetamid, fluopyram, fenfuram, furmecyclox, carboxin, oxycarboxin, thifluzamide, benzovindiflupyr, bixafen, fluxapyroxad, furametpyr, isopyrazam, penflufen, penthiopyrad, sedaxane, boscalid, and pyrapropoyne;

(c) Complex III ubiquinol oxidase Qo inhibitors: azoxystrobin, coumoxystrobin, coumethoxystrobin, enoxastrobin, flufenoxystrobin, picoxystrobin, pyraoxystrobin; pyraclostrobin, pyrametostrobin, triclopyricarb, kresoxim-methyl, trifloxystrobin, dimoxystrobin, fenaminstrobin, metominostrobin, orysastrobin, famoxadone, fluoxastrobin, fenamidone, and pyribencarb;

(d) Complex III ubiquinol reductase Qi inhibitors: cyazofamid and amisulbrom;

(e) Oxidative phosphorylation uncoupling agents: binapacryl, meptyldinocap, dinocap; fluazinam, and ferimzone;

(f) Oxidative phosphorylation inhibitors (ATP synthase inhibitors): fentin acetate, fentin chloride, and fentin hydroxide;

(g) ATP production inhibitor: silthiofam; and (h) Complex III cytochrome bcl (ubiquinone reductase) Qx (unknown) inhibitor: ametoctradin;

(4) Amino acid and protein synthesis inhibitors (a) Methionine biosynthesis inhibitors: andoprim, cyprodinil, mepanipyrim, and pyrimethanil; and (b) Protein synthesis inhibitors: blasticidin-S, kasugamycin, kasugamycin hydrochloride, streptomycin, and oxytetracycline.

(5) Signal transduction inhibitors:

(a) Signal transduction inhibitors: quinoxyfen and proquinazid; and (b) MAP/histidine kinase inhibitors in osmotic pressure signal transduction: fenpiclonil, fludioxonil, chlozolinate, iprodione, procymidone, and vinclozolin.

(6) Lipid and cell membrane synthesis inhibitors:

(a) Phospholipid biosynthesis and methyltransferase inhibitors: edifenphos, iprobenfos, pyrazophos, and isoprothiolane;

(b) Lipid peroxidation agents: biphenyl, chloroneb, dichloran, quintozene, tecnazene, tolclofos-methyl, and etridiazole;

(c) Agents that act upon cell membranes: iodocarb, propamocarb, propamocarb-hydrochloride, propamocarb-fosetylate, and prothiocarb;

(d) Microorganisms that disturb pathogen cell membranes: *Bacillus subtilis, Bacillus subtilis* strain QST713, *Bacillus subtilis* strain FZB24, *Bacillus subtilis* strain MBI600, and *Bacillus subtilis* strain D747; and (e) Agents that disturb cell membranes: *Melaleuca alternifolia* (tea tree) extract.

(7) Cell membrane sterol biosynthesis inhibitors:

(a) C14 position demethylation inhibitors in sterol biosynthesis: triforine, pyrifenox, pyrisoxazole, fenarimol, flurprimidol, nuarimol, imazalil, imazalil-sulfate, oxpoconazole, pefurazoate, prochloraz, triflumizole, viniconazole, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, fluquinconazole, simeconazole, tebuconazole, tetraconazole, triadimefon, triadimenol, triticonazole, prothioconazole, and voriconazole;

(b) Δ14 reductase and Δ8→Δ7-isomerase inhibitors in sterol biosynthesis: aldimorph, dodemorph, dodemorph acetate, fenpropimorph, tridemorph, fenpropidin, piperalin, and spiroxamine;

(c) 3-keto reductase inhibitors in C4-position demethylation in sterol biosynthesis systems: fenhexamid and fenpyrazamine; and (d) Squalene epoxidase inhibitors in sterol biosynthesis systems: pyributicarb, naftifene, and terbinafine.

(8) Cell wall synthesis inhibitors:

(a) Trehalase inhibitor: validamycin;

(b) Chitin synthase inhibitors: polyoxins and polyoxorim; and (c) Cellulose synthase inhibitors: dimethomorph, flumorph, pyrimorph, benthiavalicarb, iprovalicarb, tolprocarb, valifenalate, and mandipropamide.

(9) Melanin biosynthesis inhibitors:

(a) Reductase inhibitors in melanin biosynthesis: fthalide, pyroquilon, and tricyclazole; and (b) Anhydrase inhibitors in melanin biosynthesis: carpropamid, diclocymet, and fenoxanil.

(10) Host plant resistance-inducing agents:

(a) Agent that acts on salicylic acid biosynthetic pathway: acibenzolar-S-methyl, and (b) Others: probenazole, tiadinil, isotianil, laminarin, and *Reynoutria sachalinensis* extract.

(11) Agents for which the mode of activity is unclear: cymoxanil, fosetyl-aluminum, phosphoric acid (phosphate), tecloftalam, triazoxide, flusulfamide, diclomezine, methasulfocarb, cyflufenamid, metrafenone, pyrifenone, dodine, dodine free base, and flutianil

(12) Agents having multiple activities: copper (copper salts), bordeaux mixture, copper hydroxide, copper naphthalate, copper oxide, copper oxychloride, copper sulfate, sulfur, sulfur products, calcium polysulfide, ferbam, mancozeb, maneb, mancopper, metiram, polycarbamate, propineb, thiram, zineb, ziram, captan, captafol, folpet, chlorothalonil, dichlofluanid, tolylfluanid, guazatine, iminoctadine triacetate, iminoctadine trialbesilate, anilazine, dithianon, quinomethionate, and fluoroimide.

(13) Other agents: DBEDC, fluorofolpet, guazatine acetate, bis(8-quinolinolato) copper(II), propamidine, chloropicrin, cyprofuram, agrobacterium, bethoxazin, diphenylamine, methyl isothiocyanate (MITC), mildiomycin, capsaicin, curfraneb, cyprosulfamide, dazomet, debacarb, dichlorophen, difenzoquat, difenzoquat methyl sulfonate, flumetover, fosetyl-calcium, fosetyl-sodium, irumamycin, natamycin, nitrothal-isopropyl, oxamocarb, puropamocin sodium, pyrrolnitrin, tebufloquin, tolnifanide, zarilamide, Algophase, Amicarthiazol, Oxathiapiprolin, metiram-zinc, benthiazole, trichlamide, uniconazole, mildiomycin, Oxyfenthiin, and picarbutrazox.

Specific examples of plant growth regulators that can be mixed or used in combination with the pest control agent of the present invention are listed below.

1-methylcyclopropene, 2,3,5-triiodobenzoic acid, IAA, IBA, MCPA, MCPB, 4-CPA, 5-aminolevulinic acid hydrochloride, 6-benzylaminopurine, abscisic acid, aviglycine hydrochloride, ancymidol, butralin, calcium carbonate, calcium chloride, calcium formate, calcium peroxide, lime sulfur, calcium sulfate, chlormequat chloride, chlorpropham, choline chloride, chloroprop, cyanamide, cyclanilide, daminozide, decyl alcohol, dichlorprop, dikegulac, dimethipin, diquat, ethephon, ethychlozate, flumetralin, flurprimidol, forchlorfenuron, gibberellin A, gibberellin A3, hymexazol, inabenfide, isoprothiolane, kinetin, maleic hydrazide, mefluidide, mepiquat chloride, oxidized glutathione, paclobutrazol, pendimethalin, prohexadione-calcium, prohydrojasmon, pyraflufen-ethyl, sintofen, sodium 1-naphthaleneacetate, sodium cyanate, streptomycin, thidiazuron, triapenthenol, tribufos, trinexapac-ethyl, uniconazole P, 1-naphthylacetamide.

[Ectoparasite Control Agent]

The ectoparasite control agent of the present invention contains at least one selected from the pyridinium salts of the present invention as an active ingredient. The amount of the compound of the present invention contained in the ectoparasite control agent of the present invention is not particularly limited as long as it shows the effect of controlling ectoparasites.

Examples of host animals to be treated with the ectoparasite control agent of the present invention include warm-blooded animals including pet animals such as dogs and cats; pet birds; domestic animals such as cattle, horses, pigs and sheep; domestic fowls; and the like. In addition, honey bees, stag beetles and beetles can be exemplified.

The ectoparasite control agent of the present invention can be applied by a known veterinary method (topical, oral, parenteral or subcutaneous administration). As a method therefor, a method of orally administering tablets, capsules, mixed feeds or the like to the animals; a method of administering to the animals by using an immersion liquid, suppository, injection (intramuscular, subcutaneous, intravenous, intraperitoneal or the like) or the like; a method of topically administering by spraying, pouring-on or spotting-on an oily or aqueous liquid preparation; a method of kneading an ectoparasite control agent in a resin, molding the kneaded product into an appropriate shape such as a collar, ear tag or the like, and attaching and topically administering the resultant to the animals; and the like can be mentioned.

Ectoparasites are parasitic in and on host animals, especially warm-blooded animals. More specifically, the ectoparasites are parasitic in and on the back, armpit, lower abdomen, inner thigh and the like of the host animals and obtain nutritional sources such as blood and dandruff from the animals to live. Examples of ectoparasites include mites and ticks, lice, fleas, mosquitoes, stable flies, flesh flies and the like.

Specific examples of the ectoparasites which can be controlled by the ectoparasite control agent of the present invention are shown below.

(1) Acari

Mites belonging to the family Dermanyssidae, mites belonging to the family Macronyssidae, mites belonging to the family Laelapidae, mites belonging to the family Varroidae, mites belonging to the family Argasidae, mites belonging to the family Ixodidae, mites belonging to the family Psoroptidae, mites belonging to the family Sarcoptidae, mites belonging to the family Knemidokoptidae, mites belonging to the family Demodixidae, mites belonging to the family Trombiculidae, insect-parasitic mites such as Coleopterophagus berlesei or the like.

(2) Phthiraptera

Lice belonging to the family Haematopinidae, lice belonging to the family Linognathidae, chewing lice belonging to the family Menoponidae, chewing lice belonging to the family Philopteridae, chewing lice belonging to the family Trichodectidae;

(3) Siphonaptera

Fleas of the family Pulicidae, for example, species belonging to the genus *Ctenocephalides* (*Ctenocephalides* spp.) such as *Ctenocephalides canis* and *Ctenocephalides felis*; fleas belonging to the family Tungidae, fleas belonging to the family Ceratophyllidae, fleas belonging to the family Leptopsyllidae.

(4) Hemiptera (5) Insect pests of the order Diptera

Mosquitoes belonging to the family Culicidae, black flies belonging to the Simuliidae family, biting midges belonging to the family Ceratopogonidae, horseflies belonging to the family Tabanidae, flies belonging to the family Muscidae, tsetse flies belonging to the family Glossinidae; flesh flies belonging to the family Sarcophagidae, flies belonging to the family Hippoboscidae, flies belonging to the family Calliphoridae, flies belonging to the family Oestridae.

[Endoparasite Control- or Exterminating Agent]

The endoparasite control- or exterminating agent of the present invention contains at least one selected from the pyridinium salts of the present invention as an active ingredient. The amount of the compound of the present invention contained in the endoparasite control- or exterminating agent of the present invention is not particularly limited as long as it shows the effect of controlling endoparasites.

The parasite to be targeted by the endoparasite control- or exterminating agent of the present invention is parasitic (endoparasitic) in host animals, especially warm blooded animals and fish. Examples of host animals for which the endoparasite control- or exterminating agent of the present invention is effective include warm-blooded animals such as humans, domestic mammals (for example, cattle, horses, pigs, sheep, goats and the like), laboratory animals (for example, mice, rats, gerbils and the like), pet animals (for example, hamsters, guinea pigs, dogs, cats, horses, squirrels, rabbits, ferrets, and the like), wild and zoo mammals (monkeys, foxes, deers, buffaloes and the like), domestic fowls (turkeys, ducks, chickens, quails, geese and the like) and pet birds (pigeons, parrots, hill mynas, Java sparrows, parakeets, society finches, canaries and the like); or fish such as salmon, trout and nishikigoi. By controlling and exterminating parasites, it is possible to prevent or treat parasitic diseases mediated by the parasites.

Examples of parasites that can be controlled or exterminated include those listed below.

(1) Dioctophymatida nematodes (a) Kidney worms of the Dioctophymatidae family, for example, *Dioctophyma renale* of *Dioctophyma* spp.; and (b) Kidney worms of the Soboliphymatidae family, for example, *Soboliphyme abei* and *Soboliphyme baturini* of *Soboliphyme* spp.

(2) Trichocephalida nematodes (a) Trichina worms of the Trichinellidae family, for example, *Trichinella spiralis* of *Trichinella* spp.; and (b) Whipworms of the Trichuridae family, for example, *Capillaria annulata, Capillaria contorta, Capillaria hepatica, Capillaria perforans, Capillaria plica* and *Capillaria suis* of *Capillaria* spp.; and *Trichuris vulpis, Trichuris discolor, Trichuris ovis, Trichuris skrjabini* and *Trichuris suis* of *Trichuris* spp.

(3) Rhabditida nematodes

Threadworms of the Strongyloididae family, for example, *Strongyloides papillosus, Strongyloides planiceps, Strongyloides ransomi, Strongyloides suis, Strongyloides stercoralis, Strongyloides tumefaciens* and *Strongyloides ratti* of *Strongyloides* spp.

(4) Strongylida nematodes

Hookworms of the Ancylostomatidae family, for example, *Ancylostoma braziliense, Ancylostoma caninum, Ancylostoma duodenale* and *Ancylostoma tubaeforme* of *Ancylostoma* spp.; *Uncinaria stenocephala* of *Uncinaria* spp.; and *Bunostomum phlebotomum* and *Bunostomum trigonocephalum* of *Bunostomum* spp.

(5) Strongylida nematodes (a) Nematodes of the Angiostrongylidae family, for example, *Aelurostrongylus abstrusus* of *Aelurostrongylus* spp.; and *Angiostrongylus vasorum* and *Angiostrongylus cantonesis* of *Angiostrongylus* spp.;

(b) Nematodes of the Crenosomatidae family, for example, *Crenosoma aerophila* and *Crenosoma vulpis* of *Crenosoma* spp.;

(c) Nematodes of the Filaroididae family, for example, *Filaroides hirthi* and *Filaroides osleri* of *Filaroides* spp.;

(d) Lungworms of the Metastrongylidae family, for example, *Metastrongylus apri*, *Metastrongylus asymmetricus*, *Metastrongylus pudendotectus* and *Metastrongylus salmi* of *Metastrongylus* spp.; and (e) Gapeworms of the Syngamidae family, for example, *Cyathostoma bronchialis* of *Cyathostoma* spp.; and *Syngamus skrjabinomorpha* and *Syngamus trachea* of *Syngamus* spp.

(6) Strongylida nematodes (a) Nematodes of the Molineidae family, for example, *Nematodirus filicollis* and *Nematodirus spathiger* of *Nematodirus* spp.;

(b) Nematodes of the Dictyocaulidae family, for example, *Dictyocaulus filarial* and *Dictyocaulus viviparus* of *Dictyocaulus* spp.;

(c) Nematodes of the Haemonchidae family, for example, *Haemonchus contortus* of *Haemonchus* spp.; and *Mecistocirrus digitatus* of *Mecistocirrus* spp.;

(d) Nematodes of the Haemonchidae family, for example, *Ostertagia ostertagi* of *Ostertagia* spp.;

(e) Nematodes of the Heligmonellidae family, for example, *Nippostrongylus braziliensis* of *Nippostrongylus* spp.; and (f) Nematodes of the Trichostrongylidae family, for example, *Trichostrongylus axei*, *Trichostrongylus colubriformis* and *Trichostrongylus tenuis* of *Trichostrongylus* spp.; *Hyostrongylus rubidus* of *Hyostrongylus* spp.; and *Obeliscoides cuniculi* of *Obeliscoides* spp.

(7) Strongylida nematodes (a) Nematodes of the Chabertiidae family, for example, *Chabertia ovina* of *Chabertia* spp.; and *Oesophagostomum brevicaudatum*, *Oesophagostomum columbianum*, *Oesophagostomum dentatum*, *Oesophagostomum georgianum*, *Oesophagostomum maplestonei*, *Oesophagostomum quadrispinulatum*, *Oesophagostomum radiatum*, *Oesophagostomum venulosum* and *Oesophagostomum watanabei* of *Oesophagostomum* spp.;

(b) Nematodes of the Stephanuridae family, for example, *Stephanurus dentatus* of *Stephanurus* spp.; and (c) Nematodes of the Strongylidae family, for example, *Strongylus asini*, *Strongylus edentatus*, *Strongylus equinus* and *Strongylus vulgaris* of *Strongylus* spp.

(8) Oxyurida nematodes

Nematodes of the Oxyuridae family, for example, *Enterobius anthropopitheci* and *Enterobius vermicularis* of *Enterobius* spp.; *Oxyuris equi* of *Oxyuris* spp.; and *Passalurus ambiguus* of *Passalurus* spp.

(9) Ascaridida nemtaodes (a) Nematodes of the Ascaridiidae family, for example, *Ascaridia galli* of *Ascaridia* spp.; (b) Nematodes of the Heterakidae family, for example, *Heterakis beramporia*, *Heterakis brevispiculum*, *Heterakis gallinarum*, *Heterakis pusilla* and *Heterakis putaustralis* of *Heterakis* spp.;

(c) Nematodes of the Anisakidae family, for example, *Anisakis simplex* of *Anisakis* spp.;

(d) Nematodes of the Ascarididae family, for example, *Ascaris lumbricoides* and *Ascaris suum* of *Ascaris* spp.; and *Parascaris equorum* of *Parascaris* spp.; and (e) Nematodes of the Toxocaridae family, for example, *Toxocara canis*, *Toxocara leonina*, *Toxocara suum*, *Toxocara vitulorum* and *Toxocara cati* of *Toxocara* spp.

(10) Spirurida nematodes (a) Nematodes of the Onchocercidae family, for example, *Brugia malayi*, *Brugia pahangi* and *Brugia patei* of *Brugia* spp.; *Dipetalonema reconditum* of *Dipetalonema* spp.; *Dirofilaria immitis* of *Dirofilaria* spp.; *Filaria oculi* of *Filaria* spp.; and *Onchocerca cervicalis*, *Onchocerca gibsoni* and *Onchocerca gutturosa* of *Onchocerca* spp.

(b) Nematodes of the Setariidae family, for example, *Setaria digitata*, *Setaria equina*, *Setaria labiatopapillosa* and *Setaria marshalli* of *Setaria* spp.; and *Wuchereria bancrofti* of *Wuchereria* spp.; and (c) Nematodes of the Filariidae family, for example, *Parafilaria multipapillosa* of *Parafilaria* spp.; and *Stephanofilaria assamensis*, *Stephanofilaria dedoesi*, *Stephanofilaria kaeli*, *Stephanofilaria okinawaensis* and *Stephanofilaria stilesi* of *Stephanofilaria* spp.

(11) Spirurida nematodes (a) Nematodes of the Gnathostomatidae family, for example, *Gnathostoma doloresi* and *Gnathostoma spinigerum* of *Gnathostoma* spp.;

(b) Nematodes of the Habronematidae family, for example, *Habronema majus*, *Habronema microstoma* and *Habronema muscae* of *Habronema* spp.; and *Draschia megastoma* of *Draschia* spp.;

(c) Nematodes of the Physalopteridae family, for example, *Physaloptera canis*, *Physaloptera cesticillata*, *Physaloptera erdocyona*, *Physaloptera felidis*, *Physaloptera gemina*, *Physaloptera papilloradiata*, *Physaloptera praeputialis*, *Physaloptera pseudopraerutialis*, *Physaloptera rara*, *Physaloptera sibirica* and *Physaloptera vulpineus* of *Physaloptera* spp.;

(d) Nematodes of the Gongylonematidae family, for example, *Gongylonema pulchrum* of *Gongylonema* spp.;

(e) Nematodes of the Spirocercidae family, for example, *Ascarops strongylina* of *Ascarops* spp.; and (f) Nematodes of the Thelaziidae family, for example, *Thelazia callipaeda*, *Thelazia gulosa*, *Thelazia lacrymalis*, *Thelazia rhodesi* and *Thelazia skrjabini* of *Thelazia* spp.

[Control Agent for Other Pests]

In addition, the compounds of the present invention are excellent in the effect of controlling insect pests having a stinger or venom which harm humans and animals, insect pests that mediate various pathogens/pathogenic microbes, and insect pests that cause discomfort to humans (such as toxic pests, hygiene pests and unpleasant pests).

Specific examples of these other pests are listed below.

(1) Hymenoptera Insect Pests

Sawflies of the Argidae family, wasps of the Cynipidae family, sawflies of the Diprionidae family, ants of the Formicidae family, wasps of the Mutillidae vamily family, and wasps of the Vespidae family.

(2) Other Insect Pests

Blattodea, termites, Araneae, centipedes, millipedes, crustacea and *Cimex lectularius*.

EXAMPLES

[Pharmaceutical Formulation]

Although some pharmaceutical formulations of the pest control agent, insecticidal or acaricidal agent, ectoparasite control agent, or endoparasite control- or exterminating agent of the present invention are shown, additives and the addition ratios should not be limited to these examples and can be modified over a wide range. The term "part" in the formulations indicates "part by weight".

The formulations for agricultural and horticultural use and for paddy rice are shown below.

(Formulation 1: Wettable Powder)

40 parts of the compound of the present invention, 53 parts of diatomaceous earth, 4 parts of a higher alcohol sulfuric acid ester and 3 parts of an alkyl naphthalene sulfonate are uniformly mixed and finely pulverized to obtain a wettable powder containing 40% of an active ingredient.

(Formulation 2: Emulsion)

30 parts of the compound of the present invention, 33 parts of xylene, 30 parts of dimethylformamide and 7 parts of a polyoxyethylene alkyl allyl ether are mixed and dissolved to obtain an emulsion containing 30% of an active ingredient.

(Formulation 3: Granule)

5 parts of the compound of the present invention, 40 parts of talc, 38 parts of clay, 10 parts of bentonite and 7 parts of a sodium alkylsulfate are uniformly mixed and finely pulverized, and then granulated into a granular form having a diameter of 0.5 to 1.0 mm to obtain a granule containing 5% of an active ingredient.

(Formulation 4: Granule)

5 parts of the compound of the present invention, 73 parts of clay, 20 parts of bentonite, 1 part of sodium dioctyl sulfosuccinate and 1 part of potassium phosphate are thoroughly ground and mixed, water is added and thoroughly kneaded, followed by granulation and drying to obtain a granule containing 5% of an active ingredient.

(Formulation 5: Suspension)

10 parts of the compound of the present invention, 4 parts of a polyoxyethylene alkyl allyl ether, 2 parts of a polycarboxylic acid sodium salt, 10 parts of glycerin, 0.2 parts of xanthan gum and 73.8 parts of water are mixed and subjected to wet grinding until the particle size becomes 3 microns or less to obtain a suspension containing 10% of an active ingredient.

The formulations of an ectoparasite control agent or an endoparasite control- or exterminating agent are shown below.

(Formulation 6: Granule)

5 parts of the compound of the present invention are dissolved in an organic solvent to obtain a solution, the solution is sprayed onto 94 parts of kaolin and 1 part of white carbon, and then the solvent is evaporated under reduced pressure. This type of granule can be mixed with animal feed.

(Formulation 7: Injection)

0.1 to 1 part of the compound of the present invention and 99 to 99.9 parts of peanut oil are uniformly mixed and then sterilized by filtration through a sterilizing filter.

(Formulation 8: Pour-on Agent)

5 parts of the compound of the present invention, 10 parts of a myristic acid ester and 85 parts of isopropanol are uniformly mixed to obtain a pour-on agent.

(Formulation 9: Spot-on Agent)

10 to 15 parts of the compound of the present invention, 10 parts of a palmitic acid ester and 75 to 80 parts of isopropanol are uniformly mixed to obtain a spot-on agent.

(Formulation 10: Spraying Agent)

1 part of the compound of the present invention, 10 parts of propylene glycol and 89 parts of isopropanol are uniformly mixed to obtain a spraying agent.

Next, the present invention will be described in more detail by showing synthesis examples. However, the present invention is in no way limited by the following examples.

Example 1

Production of Inner Salt of 1-((2E)-3-(4-(4-trifluoromethyl) phenyl) phenyl-2-propenamide)-4-(trifluoromethyl) pyridinium

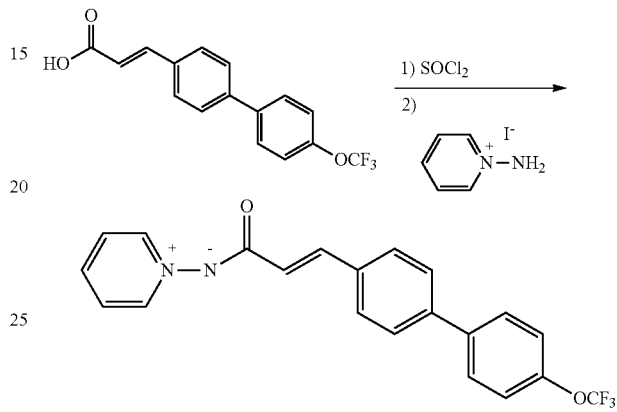

Thionyl chloride (0.09 g), toluene (3 ml) and pyridine (one drop) were added to (2E)-3-(4-(4-(trifluoromethyl) phenyl) phenyl-2-propenoic acid (0.07 g), and the resulting mixture was reacted at 70° C. for 30 minutes. The reaction solution was allowed to cool and then the solvent was distilled off, chloroform (10 ml), 1-aminopyridinium iodide (0.05 g) and triethylamine (0.07 g) were added to the residue, and the resulting mixture was stirred at room temperature for 13 hours. Thereafter, the resultant was extracted with 2N hydrochloric acid, and a 10% sodium hydroxide aqueous solution was added to the obtained aqueous layer until the pH reached 11. The resultant was extracted with chloroform, washed with water and then dried over anhydrous magnesium sulfate. The chloroform was distilled off to obtain the desired product (0.09 g).

1-aminopyridinium iodide was prepared by the method described in Organic Syntheses Collective Volume V. p. 43 (1973).

Example 2

Production of Inner Salt of 1-(4-(4-(trifluoromethoxy) phenyl) benzamide) pyridinium

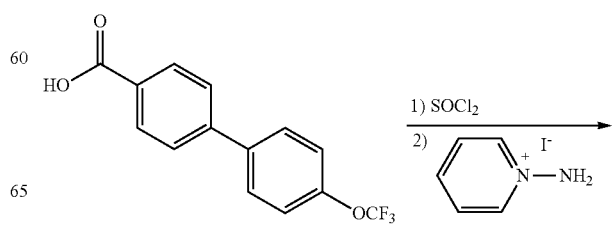

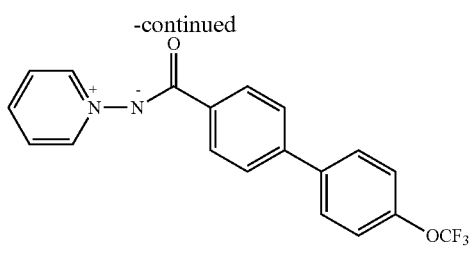

Thionyl chloride (0.86 g), toluene (15 ml) and pyridine (one drop) were added to 4-(4-(trifluoromethoxy) phenyl) benzoic acid (0.64 g), and the resulting mixture was refluxed for 1 hour. The reaction solution was allowed to cool and then the solvent was distilled off, chloroform (15 ml), N-aminopyridinium iodide (0.53 g) and triethylamine (0.73 g) were added to the residue, and the resulting mixture was stirred at room temperature for 17 hours. Thereafter, the resultant was charged into an appropriate amount of water. After that, the resultant was extracted with chloroform. The organic layer was dried over anhydrous magnesium sulfate, then the solvent was distilled off, and the obtained solid was washed with diethyl ether to obtain the desired product (0.45 g).

Example 3

Production of 1-((2E)-3-(4-(4-(trifluoromethoxy) phenyl) phenyl)-2-propenamide) pyridinium chloride

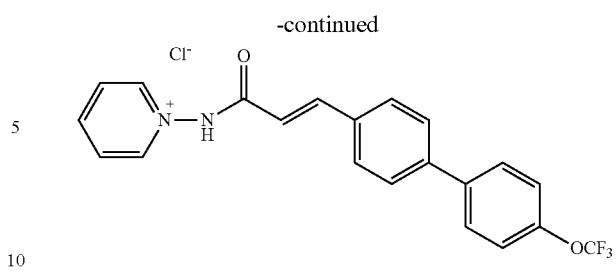

2N hydrochloric acid (20 ml) was added to an inner salt of 1-((2E)-3-(4-(4-trifluoromethoxy) phenyl) phenyl-2-propenamide) pyridinium (0.38 g), and the resulting mixture was stirred at room temperature for 6.5 hours. Hydrochloric acid was distilled off from the resulting solution to thereby obtain the desired product (0.15 g).

Examples of the compounds of the present invention prepared by the same method as in the above Examples are shown in Tables 1 to 4. Physical property data of the compounds were entered in the column of "Physical properties". As the physical property data, properties or melting points (m.p.) were described. In Tables 1 to 4, Me represents a methyl group, Ph represents a phenyl group, $^i$Pr represents an i-propyl group, $^t$Bu represents a t-butyl group and Et represents an ethyl group.

Table 1 shows the compounds represented by the formula (I-a) among the compounds of the present invention. The bond marked with the symbol * used for the notation of Y is bonded to the carbonyl group in the pyridinium salt.

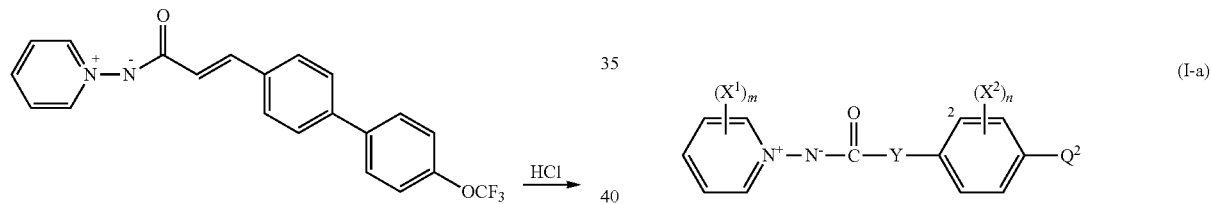

TABLE 1

| Compound No. | $(X^1)m$ | Y | $(X^2)n$ | $Q^2$ | Physical properties |
|---|---|---|---|---|---|
| a-1 | — | ![](H/*=/OMe) | — | 4-CF$_3$Ph | m.p. 177-179° C. |
| a-2 | — | ![](H/*=/S(=O)Me) | — | 4-CF$_3$OPh | m.p. 150-151° C. |
| a-3 | — | ![](H/*=/SO$_2$Me) | — | 4-CF$_3$OPh | m.p. 83-85° C. |

TABLE 1-continued
| Compound No. | (X¹)m | Y | (X²)n | Q² | Physical properties |
|---|---|---|---|---|---|
| a-4 | — | 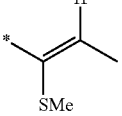 | — | 4-CF₃OPh | m.p. 133-135° C. |
| a-5 | — | 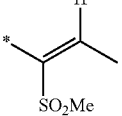 | — | 4-CF₃Ph | m.p. 178-180° C. |
| a-6 | — | 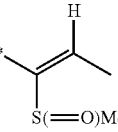 | — | 4-CF₃Ph | m.p. 203-205° C. |
| a-7 | — | 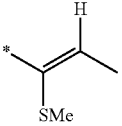 | — | 4-CF₃Ph | m.p. 164-166° C. |
| a-8 | — | 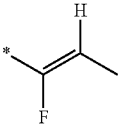 | — | 4-CF₃Ph | m.p. 250° C. |
| a-9 | — | 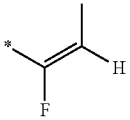 | — | 4-CF₃Ph | m.p. 125-126° C. |
| a-10 | — | 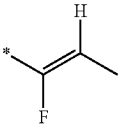 | — | 4-CF₃OPh | m.p. 233-236° C. |
| a-11 | — | 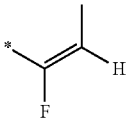 | — | 4-CF₃OPh | m.p. 117-118° C. |
| a-12 | — | — | — | 4-(5-CF₃-Pyridin-2-yl)OPh | m.p. 204-205° C. |
| a-13 | — | — | — | 4-(2-CF₃-Thiazol-4-yl)-Ph | m.p. 225-228° C. |
| a-14 | — | — | — | 4-(2-Me-Thiazol-4-yl)-Ph | m.p. 265-268° C. |
| a-15 | — | — | — | 4-CF₃CH₂OPh | m.p. 226-228° C. |
| a-16 | — | 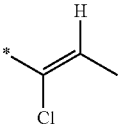 | — | 4-CF₃OPh | m.p. 163-165° C. |
| a-17 | — | 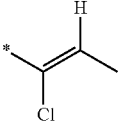 | — | 4-CF₃Ph | m.p. 204-206° C. |
| a-18 | — | — | — | 4-$^i$PrPh | m.p. 186-188° C. |
| a-19 | — | — | — | 4-$^t$BuPh | m.p. 185-187° C. |

TABLE 1-continued

| Compound No. | (X¹)m | Y | (X²)n | Q² | Physical properties |
|---|---|---|---|---|---|
| a-20 | — | — | — | 4-(1-Me-3-$CF_3$-1H-Pyrazol-5-yl)-Ph | m.p. 253-255° C. |
| a-21 | — | — | — | 4-(1-Me-3-$CF_3$-1H-Pyrazol-5-yl)-Ph | m.p. 229-232° C. |
| a-22 | — | — | — | 4-(4-$CF_3$OPh)$CH_2$OPh | m.p. 210-212° C. |
| a-23 | — | — | — | 4-(4-$CF_3$OPh)$CH_2$OPh | m.p. 250° C. |
| a-24 | — | — | — | 3-(3-$CF_3$-Isoxazol-5-yl)-Ph | m.p. 255-259° C. |
| a-25 | — | — | — | 4-(5-$CF_3$-Pyridin-2-yl)-Ph | m.p. 259-264° C. |
| a-26 | — | — | — | 3-(5-Me-1,2,4-Oxadiazol-3-yl)-Ph | m.p. 224-228° C. |
| a-27 | — | — | — | 2-Cl-4-$CF_3$O—Ph | m.p. 160-161° C. |
| a-28 | — | — | — | 3-Cl-4-$CF_3$O—Ph | m.p. 173-175° C. |
| a-29 | — | — | — | 2,3,5,6-$F_4$-4-$CF_3$—Ph | m.p. 214-216° C. |
| a-30 | — | — | — | 4-$CF_3$C≡C—Ph | m.p. 210-213° C. |
| a-31 | — | — | — | 4-EtOC(=O)Ph | m.p. 189-191° C. |
| a-32 | — | — | — | 4-$CHF_2$OPh | m.p. 224-226° C. |
| a-33 | — | — | — | 4-$CF_3SO_3$Ph | m.p. 214-216° C. |
| a-34 | — | — | — | 4-$^i$PrOPh | m.p. 197-200° C. |
| a-35 | — | — | — | 4-HOPh | m.p. 250° C. |
| a-36 | — | — | — | 4-$CF_3$SPh | m.p. 163-166° C. |
| a-37 | — | — | 2-F | 4-$CF_3$OPh | m.p. 110-113° C. |
| a-38 | — | — | 2-F | 4-$CF_3$Ph | m.p. 125-128° C. |
| a-39 | — | — | — | 3-F-4-$CF_3$O—Ph | m.p. 217-218° C. |
| a-40 | 3,4-$Me_2$ | — | — | 4-$CF_3$OPh | m.p. 243-245° C. |
| a-41 | — | — | 2-Me | 4-$CF_3$OPh | m.p. 144-146° C. |
| a-42 | — | — | 2-Me | 4-$CF_3$Ph | m.p. 164-167° C. |
| a-43 | — | — | 3-Me | 4-$CF_3$OPh | m.p. 182-185° C. |
| a-44 | — | — | 3-Me | 4-$CF_3$Ph | m.p. 195-197° C. |
| a-45 | — | — | — | 4-$CF_3$OPh | m.p. 170-172° C. |
| a-46 | 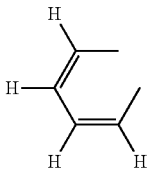 | — | — | 4-$CF_3$OPh | m.p. 186-189° C. |
| a-47 | 4-MeO | — | — | 4-$CF_3$OPh | m.p. 145-147° C. |
| a-48 | 4-$Me_2$N | — | — | 4-$CF_3$OPh | m.p. 220-223° C. |
| a-49 | — | — | 3-F | 4-$CF_3$Ph | m.p. 218-220° C. |
| a-50 | — | — | 3-F | 4-$CF_3$OPh | m.p. 208-210° C. |
| a-51 | — | 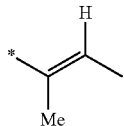 | — | 4-$CF_3$OPh | m.p. 162-165° C. |
| a-52 | — | 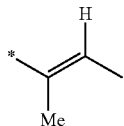 | — | 4-$CF_3$Ph | m.p. 200-203° C. |
| a-53 | — | 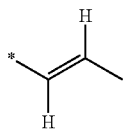 | — | 4-$CF_3$OPh | m.p. 178-181° C. |
| a-54 | 4-$CF_3$ | 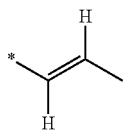 | — | 4-$CF_3$Ph | m.p. 249-252° C. |
| a-55 | 4-$CF_3$ | — | — | 4-$CF_3$Ph | m.p. 222-225° C. |
| a-56 | — | — | — | 4-(4-$CF_3$Ph)—Ph | m.p. 250° C. |
| a-57 | — | — | — | 4-BrPh | m.p. 237-240° C. |
| a-58 | 3-Cl | — | — | 4-$CF_3$Ph | m.p. 213-215° C. |
| a-59 | — | — | — | 4-$CF_3$OPh | m.p. 194-195° C. |

TABLE 1-continued

| Compound No. | (X¹)m | Y | (X²)n | Q² | Physical properties |
|---|---|---|---|---|---|
| a-60 | — | *-CH=CH-CH₃ (with H's shown) | — | 4-CF₃Ph | m.p. 201-204° C. |
| a-61 | — | *-CH=CH-CH₃ (with H's shown) | — | 4-ClPh | m.p. 227-229° C. |
| a-62 | — | — | — | 4-CF₃Ph | m.p. 151-154° C. |
| a-63 | — | — | — | 3-CF₃Ph | m.p. 167-170° C. |
| a-64 | — | — | — | Ph | m.p. 201-204° C. |
| a-65 | — | — | — | 4-CF₃Ph | m.p. 228-230° C. |
| a-66 | — | — | — | 4-CNPh | m.p. 250° C. |
| a-67 | — | — | — | 4-ClPh | m.p. 212-214° C. |
| a-68 | — | — | — | 6-$^i$PrO-Pyridin-3-yl | m.p. 172-176° C. |
| a-69 | — | — | — | 6-CF₃CH₂O-Pyridin-3-yl | m.p. 207-209° C. |
| a-70 | — | — | — | 2-CF₃-Thiazol-4-yl | m.p. 228-230° C. |
| a-71 | — | — | — | 1-Me-3-CF₃-1H-Pyrazol-5-yl | m.p. 191-193° C. |
| a-72 | — | — | — | 1-Me-5-CF₃-1H-Pyrazol-3-yl | m.p. 239-241° C. |
| a-73 | — | — | — | 3-CF₃-Isoxazol-5-yl | m.p. 263-266° C. |
| a-74 | — | — | — | 5-$^t$Bu-1,2,4-Oxadiazol-3-yl | m.p. 150-152° C. |
| a-75 | — | — | — | 3-F-4-CF₃—Ph | m.p. 250° C. |
| a-76 | — | — | — | 3-Cl-4-CF₃CH₂O-5-Me—Ph | m.p. 189-191° C. |
| a-77 | — | — | — | 3-Me-4-CF₃CH₂O—Ph | m.p. 183-185° C. |
| a-78 | — | — | — | 3-Cl-4-CF₃CH₂O—Ph | m.p. 192-194° C. |
| a-79 | — | — | — | 1-CF₃CH₂-1H-Pyrazol-4-yl | m.p. 234-236° C. |
| a-80 | — | — | — | 3,5-Me₂-4-CF₃CH₂O—Ph | m.p. 138-140° C. |
| a-81 | — | — | — | 3-MeO-4-CF₃CH₂O—Ph | m.p. 130-132° C. |
| a-82 | — | — | — | 3-F-4-CF₃CH₂O—Ph | m.p. 146-148° C. |
| a-83 | — | — | — | 4-CF₃CFHCF₂OPh | m.p. 225-226° C. |
| a-84 | — | — | 3-Cl | 4-CF₂HCF₂OPh | m.p. 148-150° C. |
| a-85 | — | — | 3-Cl | 4-CF₃OPh | m.p. 136-138° C. |
| a-86 | — | — | 3-F | 4-CF₃CH₂OPh | m.p. 160-162° C. |
| a-87 | — | — | 3-F | 4-CF₂HCH₂OPh | m.p. 62-64° C. |
| a-88 | — | — | — | 5-CF₃CH₂O-Pyridin-2-yl | m.p. 189-190° C. |
| a-89 | — | — | 3-NO₂ | 4-CF₃OPh | nD(21.7° C.) 1.5421 |
| a-90 | — | — | — | 4-CF₂HCH₂OPh | m.p. 170-172° C. |
| a-91 | — | — | 3-F | 4-CF₂HCF₂CH₂OPh | m.p. 90-92° C. |
| a-92 | — | — | 3-F | 4-CF₂HCF₂OPh | m.p. 108-110° C. |
| a-93 | — | — | — | 3-Cl-4-CF₃—Ph | m.p. 224-226° C. |
| a-94 | — | — | — | 2-F-4-CF₃—Ph | m.p. 277-279° C. |
| a-95 | 2-Me | — | — | 4-CF₂HCF₂OPh | m.p. 130-132° C. |
| a-96 | 2-Me | — | — | 4-CF₃OPh | m.p. 112-114° C. |
| a-97 | — | — | — | 4-CF₃CF₂OPh | m.p. 193-195° C. |
| a-98 | — | — | — | 4-CF₃CF₂CF₂Ph | m.p. 185-187° C. |
| a-99 | — | — | — | 4-SF₅Ph | m.p. 194-196° C. |
| a-100 | — | — | — | 4-CF₃CF₂CF₂CH₂OPh | m.p. 177-181° C. |
| a-101 | — | — | — | 4-CF₃CF₂CH₂OPh | m.p. 200-204° C. |
| a-102 | — | — | — | 4-MeSO₂Ph | m.p. 250° C. |
| a-103 | — | — | — | 4-NMe₂Ph | m.p. 250° C. |
| a-104 | — | — | — | 4-CF₂HCF₂CH₂OPh | m.p. 224-226° C. |
| a-105 | — | — | — | 4-CF₃HCF₂OPh | m.p. 206-208° C. |
| a-106 | — | — | — | 4-CF₃CF₂Ph | m.p. 220-222° C. |
| a-107 | — | — | — | 4-CF₂HPh | m.p. 245-247° C. |
| a-108 | — | — | — | 3-Me-4-CF₃—Ph | m.p. 210-212° C. |
| a-109 | — | — | — | 4-$^c$PrOPh | m.p. 200-202° C. |
| a-110 | — | — | — | 4-(2,2-F₂—$^c$Pr)—Ph | m.p. 180-182° C. |
| a-111 | — | — | — | 4-(2,2-Cl₂—$^c$Pr)—Ph | m.p. 130-132° C. |
| a-112 | — | — | — | 6-CF₃O-Pyridin-3-yl | m.p. 249-251° C. |
| a-113 | — | — | — | 3-CF₃OPh | m.p. 154-156° C. |
| a-114 | — | — | — | 2-CF₃OPh | m.p. 148-150° C. |
| a-115 | — | — | — | 4-FPh | m.p. 242-244° C. |

TABLE 1-continued

| Compound No. | (X¹)m | Y | (X²)n | Q² | Physical properties |
|---|---|---|---|---|---|
| a-116 | — | CH=C(H)(Me) with OEt on * carbon | — | 4-CF$_3$OPh | m.p. 198-200° C. |
| a-117 | — | CH=C(H)(Me) with OMe on * carbon | — | 4-CF$_3$OPh | m.p. 194-196° C. |
| a-118 | — | CH=C(H)(Me) with Br on * carbon | — | 4-CF$_3$OPh | m.p. 128-130° C. |
| a-119 | — | CH=C(H)(Me) with Et on * carbon | — | 4-CF$_3$OPh | m.p. 110-112° C. |
| a-120 | — | — | — | 2-Me-4-CF$_3$CH$_2$O—Ph | m.p. 161-163° C. |
| a-121 | — | — | — | 2-Cl-4-CF$_3$CH$_2$O—Ph | m.p. 192-194° C. |
| a-122 | — | — | — | 2-F-4-CF$_3$CH$_2$O—Ph | m.p. 221-223° C. |
| a-123 | — | — | — | 2-CF$_3$-1H-Pyrazol-1-yl | m.p. 247-249° C. |
| a-124 | — | — | — | 4-CF$_3$-1H-Pyrazol-1-yl | m.p. 264-266° C. |
| a-125 | — | — | — | 4-CF$_3$-1H-Imidazol-1-yl | m.p. 290-292° C. |

Examples of the compounds of the present invention are further shown. Table 2 shows the compounds represented by formula (I'). The bond marked with the symbol * used for the notation of Q¹-Q² is bonded to the carbonyl group in the pyridinium salt.

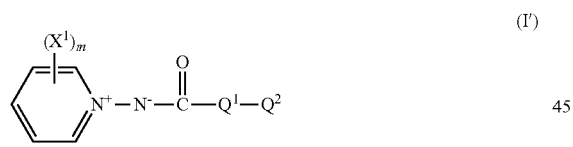

(I')

TABLE 2

| Compound No. | (X¹)m | Q¹-Q² | Physical properties |
|---|---|---|---|
| b-1 | — | 2-(3-CF$_3$-phenyl)pyridin-6-yl | m.p. 41-43° C. |
| b-2 | — | 6-(4-OCF$_3$-phenyl)-1H-indol-2-yl | m.p. 272-275° C. |

TABLE 2-continued
| Compound No. | (X¹)m | Q¹-Q² | Physical properties |
|---|---|---|---|
| b-3 | — | 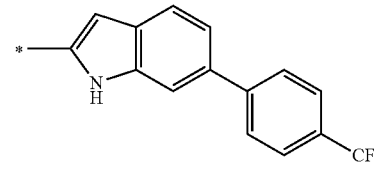 | m.p. 290-292° C. |
| b-4 | — | 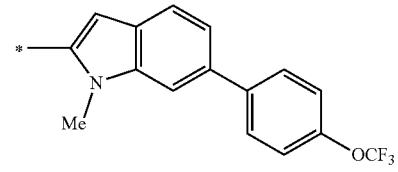 | m.p. 144-147° C. |
| b-5 | — | 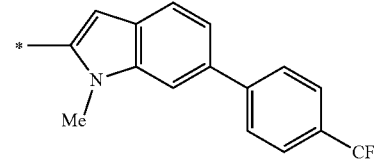 | m.p. 198-200° C. |
| b-6 | — | 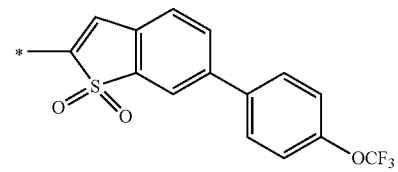 | m.p. 238-240° C. |
| b-7 | — | 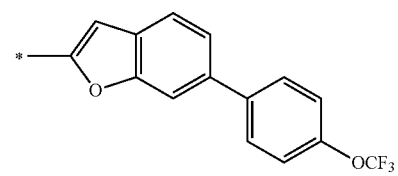 | m.p. 172-174° C. |
| b-8 | — | 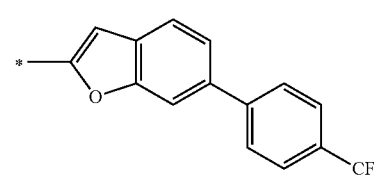 | m.p. 186-189° C. |
| b-9 | — | 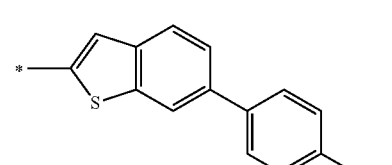 | m.p. 251-253° C. |
| b-10 | — | 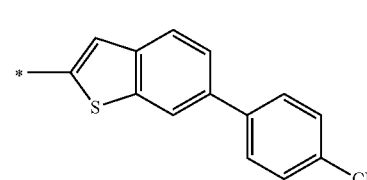 | m.p. 263-265° C. |
| b-11 | — | 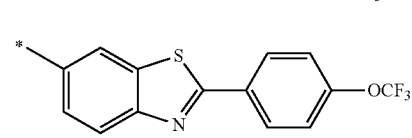 | m.p. 215-217° C. |

TABLE 2-continued
| Compound No. | (X¹)m | Q¹-Q² | Physical properties |
|---|---|---|---|
| b-12 | — | 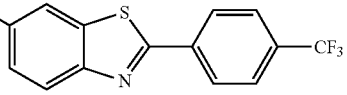 | m.p. 264-266° C. |
| b-13 | — | 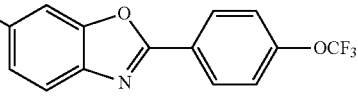 | m.p. 193-194° C. |
| b-14 | — | 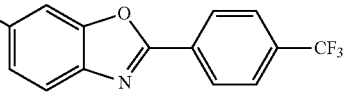 | m.p. 248-250° C. |
| b-15 | — | 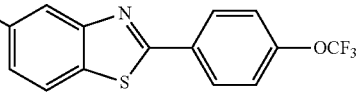 | m.p. 211-213° C. |
| b-16 | — | 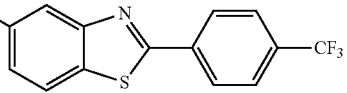 | m.p. 256-259° C. |
| b-17 | — | 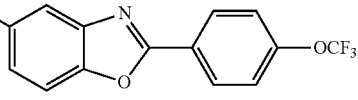 | m.p. 187-189° C. |
| b-18 | — | 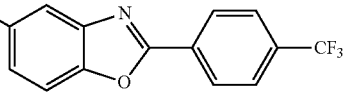 | m.p. 227-231° C. |
| b-19 | — | 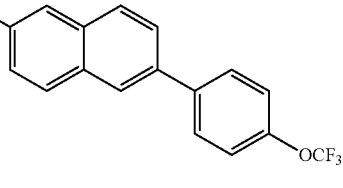 | m.p. 208-211° C. |
| b-20 | — | 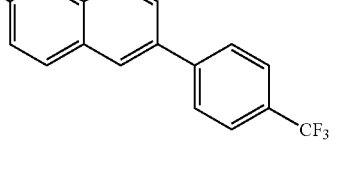 | m.p. 234-237° C. |
| b-21 | — | 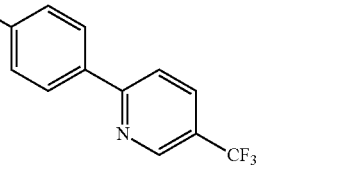 | m.p. 242-248° C. |

TABLE 2-continued
| Compound No. | (X¹)m | Q¹-Q² | Physical properties |
|---|---|---|---|
| b-22 | — | 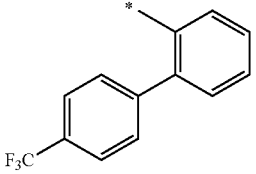 | amorphous |
| b-23 | — | 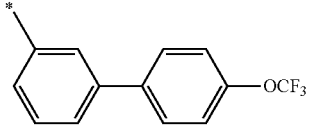 | nD(21.5° C.)1.529 |
| b-24 | — | 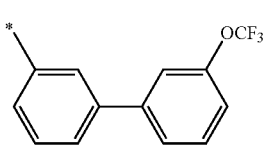 | nD(21.6° C.)1.537 |
| b-25 | — | 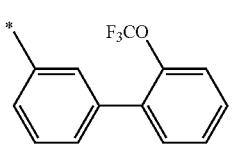 | m.p. 106-108° C. |
| b-26 | — | 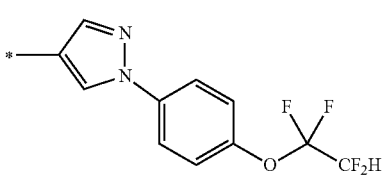 | m.p. 142-145° C. |
| b-27 | — | 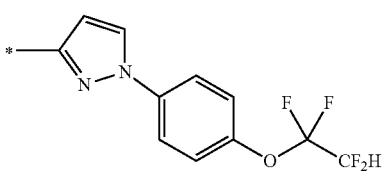 | m.p. 153-156° C. |
| b-28 | — | 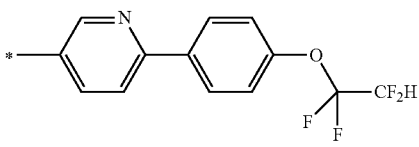 | m.p. 206-208° C. |
| b-29 | — | 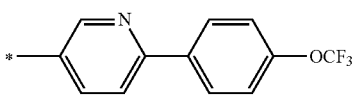 | m.p. 221-222° C. |
| b-30 | — | 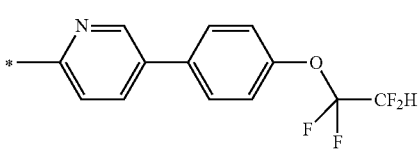 | m.p. 199-203° C. |
| b-31 | — | 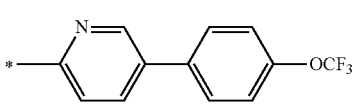 | m.p. 236-238° C. |

TABLE 2-continued

| Compound No. | (X¹)m | Q¹-Q² | Physical properties |
|---|---|---|---|
| b-32 | — | 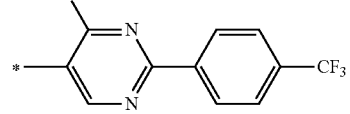 | m.p. 177-180° C. |
| b-33 | — | 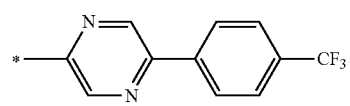 | m.p. 238-240° C. |
| b-34 | — | 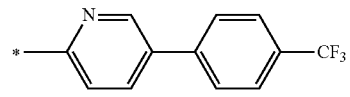 | m.p. 262-264° C. |
| b-35 | — | 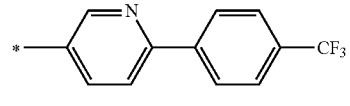 | m.p. 259-261° C. |
| b-36 | — | 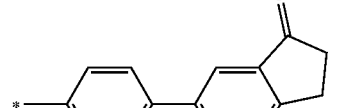 | m.p. 250° C. |

Examples of the compounds of the present invention are further shown. Table 3 shows the compounds represented by the formula (II-a). The bond marked with the symbol * used for the notation of Y is bonded to the carbonyl group in the pyridinium salt. In Table 3, "Tol" represents a tolyl group.

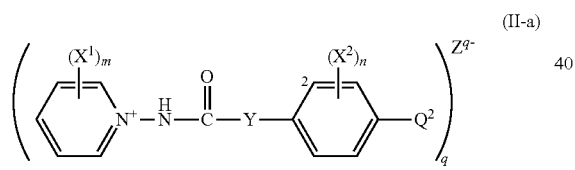

(II-a)

TABLE 3

| Compound No. | (X¹)m | Y | (X²)n | Q² | q | $Z^{q-}$ | Physical properties |
|---|---|---|---|---|---|---|---|
| c-1 | — | — | — | 4-CF₃OPh | 1 | Tol-SO₃⁻ | m.p. 246-249° C. |
| c-2 | — | — | — | 4-CF₃OPh | 2 | SO₄²⁻ | m.p. 237-240° C. |
| c-3 | — | — | — | 4-CF₃OPh | 1 | MeSO₃⁻ | m.p. 202-204° C. |
| c-4 | — | — | — | 4-CF₃OPh | 1 | Br⁻ | m.p. 250° C. |
| c-5 | — | — | — | 4-CF₃OPh | 1 | I⁻ | m.p. 140-141° C. |
| c-6 | — | 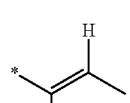 | — | 4-ClPh | 1 | Cl⁻ | m.p. 229-232° C. |
| c-7 | — | — | — | 4-CF₃Ph | 1 | Cl⁻ | m.p. 204-207° C. |
| c-8 | — | — | — | 4-ClPh | 1 | Cl⁻ | m.p. 212-215° C. |
| c-9 | — | — | — | 2-CF₃Ph | 1 | Cl⁻ | m.p. 205-208° C. |
| c-10 | — | — | — | Ph | 1 | Cl⁻ | m.p. 201-203° C. |

TABLE 3-continued

| Compound No. | $(X^1)_m$ | Y | $(X^2)_n$ | $Q^2$ | q | $Z^{q-}$ | Physical properties |
|---|---|---|---|---|---|---|---|
| c-11 | — | 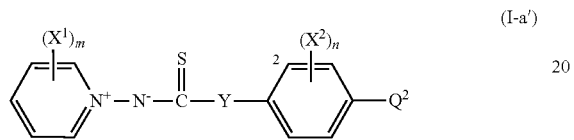 | — | 4-CF$_3$OPh | 1 | Cl$^-$ | m.p. 228-231° C. |
| c-12 | — | — | — | 4-CF$_3$OPh | 1 | Cl$^-$ | m.p. 223-225° C. |

Examples of the compounds of the present invention are further shown. Table 4 shows the compounds represented by formula (I-a').

(I-a')

TABLE 4

| Compound No. | $(X^1)_m$ | Y | $(X^2)_n$ | $Q^2$ | Physical property values |
|---|---|---|---|---|---|
| d-1 | 2-Me | — | — | 4-CF$_2$HCF$_2$OPh | m.p. 167-169° C. |
| d-2 | 2-Me | — | — | 4-CF$_3$OPh | m.p. 158-160° C. |
| d-3 | — | — | — | 4-CF$_3$OPh | m.p. 200° C. |

[Biological Test]

The following test examples show that the compounds of the present invention are useful as active ingredients of pest control agents. "Parts" are on a weight basis.

(Preparation of Test Emulsion)

5 parts by weight of the compound of the present invention, 93.6 parts by weight of dimethylformamide, and 1.4 parts by weight of polyoxyethylene alkylaryl ether were mixed and dissolved to prepare an emulsion (1) containing 5% of an active ingredient.

98.6 parts by weight of dimethylformamide, and 1.4 parts by weight of polyoxyethylene alkylaryl ether were mixed and dissolved to prepare an emulsion (11) containing no active ingredient.

(Test Example 1) Efficacy Test Against *Mythimna separata*

The emulsion (1) was diluted with water so that the concentration of the compound of the present invention was 125 ppm. Maize leaf pieces were immersed in the diluent for 30 seconds. The maize leaf pieces were placed in a petri dish, and five second instar larvae of *M. separata* were released.

The petri dish was left to stand in a thermostatic chamber at a temperature of 25° C. and a humidity of 60% during the test period. Mortality was evaluated when 6 days passed since the release of the insects, and the insecticidal rate was calculated. The test was repeated twice.

The compounds shown in Table 5 were tested for efficacy against *M. separata*. All compounds showed an insecticidal rate of 80% or more against *M. separata*. The insecticidal rate of the compound represented by formula (A) (sometimes referred to as comparative compound A) described in Patent Document 1 was 0%.

TABLE 5

| Compound No. |
|---|
| a-1 |
| a-4 |
| a-7 |
| a-8 |
| a-9 |
| a-10 |
| a-11 |
| a-12 |
| a-13 |
| a-15 |
| a-16 |
| a-17 |
| a-18 |
| a-19 |
| a-20 |
| a-21 |
| a-24 |
| a-25 |
| a-26 |
| a-27 |
| a-28 |
| a-30 |
| a-32 |
| a-33 |
| a-34 |
| a-36 |
| a-37 |
| a-38 |
| a-39 |
| a-40 |
| a-42 |
| a-43 |
| a-44 |
| a-45 |
| a-46 |
| a-47 |
| a-49 |
| a-50 |
| a-51 |
| a-52 |
| a-53 |
| a-55 |
| a-56 |
| a-57 |
| a-59 |
| a-60 |
| a-61 |
| a-63 |
| a-65 |
| a-67 |
| a-68 |
| a-69 |
| a-77 |
| a-80 |
| a-81 |
| a-82 |
| a-84 |
| a-85 |
| a-86 |
| a-87 |
| a-88 |
| a-90 |

TABLE 5-continued

| Compound No. |
|---|
| a-91 |
| a-92 |
| a-93 |
| a-94 |
| a-95 |
| a-98 |
| a-100 |
| a-101 |
| a-103 |
| a-104 |
| a-105 |
| a-106 |
| a-107 |
| a-108 |
| a-109 |
| a-110 |
| a-111 |
| a-113 |
| a-115 |
| a-116 |
| a-117 |
| a-118 |
| a-119 |
| b-4 |
| b-5 |
| b-7 |
| b-8 |
| b-9 |
| b-10 |
| b-11 |
| b-12 |
| b-13 |
| b-14 |
| b-15 |
| b-16 |
| b-17 |
| b-18 |
| b-19 |
| b-20 |
| b-21 |
| b-29 |
| b-30 |
| b-32 |
| b-35 |
| c-1 |
| c-2 |
| c-3 |
| c-4 |
| c-6 |
| c-7 |
| c-8 |
| c-11 |
| c-12 |
| d-1 |
| d-2 |
| d-3 |

(Test Example 2) Efficacy Test Against *Spodoptera litura*

The emulsion (1) was diluted with water so that the concentration of the compound of the present invention was 125 ppm. Cabbage leaves were immersed in the diluent for 30 seconds. The cabbage leaves were placed in a petri dish, and five second instar larvae of *S. litura* were released. The petri dish was left to stand in a thermostatic chamber at a temperature of 25° C. and a humidity of 60% during the test period. Mortality was evaluated when 6 days passed since the release of the insects, and the insecticidal rate was calculated. The test was repeated twice.

The compounds shown in Table 6 were tested for efficacy against *S. litura*. All compounds showed an insecticidal rate of 80% or more against *S. litura*. The insecticidal rate of the comparative compound A was 0%.

TABLE 6

| Compound No. |
|---|
| a-1 |
| a-4 |
| a-7 |
| a-8 |
| a-9 |
| a-10 |
| a-11 |
| a-12 |
| a-13 |
| a-15 |
| a-16 |
| a-17 |
| a-18 |
| a-19 |
| a-20 |
| a-21 |
| a-24 |
| a-25 |
| a-26 |
| a-27 |
| a-28 |
| a-30 |
| a-32 |
| a-33 |
| a-34 |
| a-36 |
| a-37 |
| a-38 |
| a-39 |
| a-40 |
| a-42 |
| a-43 |
| a-44 |
| a-45 |
| a-46 |
| a-47 |
| a-49 |
| a-50 |
| a-51 |
| a-52 |
| a-53 |
| a-55 |
| a-56 |
| a-59 |
| a-60 |
| a-61 |
| a-68 |
| a-69 |
| a-76 |
| a-77 |
| a-78 |
| a-81 |
| a-82 |
| a-83 |
| a-84 |
| a-86 |
| a-87 |
| a-90 |
| a-91 |
| a-92 |
| a-95 |
| a-97 |
| a-98 |
| a-100 |
| a-101 |
| a-104 |
| a-105 |
| a-106 |
| a-108 |
| a-109 |
| a-110 |
| a-111 |
| a-116 |
| a-117 |
| a-118 |
| a-119 |
| b-4 |
| b-5 |

TABLE 6-continued

| Compound No. |
| --- |
| b-7 |
| b-8 |
| b-9 |
| b-10 |
| b-11 |
| b-12 |
| b-13 |
| b-14 |
| b-15 |
| b-16 |
| b-17 |
| b-18 |
| b-19 |
| b-20 |
| b-30 |
| c-1 |
| c-2 |
| c-3 |
| c-4 |
| c-6 |
| c-7 |
| c-8 |
| c-11 |
| c-12 |
| d-1 |

(Test Example 3) Efficacy Test Against *Plutella xylostella*

The emulsion (I) was diluted with water so that the concentration of the compound of the present invention was 125 ppm. Cabbage leaves were immersed in the diluent for 30 seconds. The cabbage leaves were air dried and placed in a petri dish, and five second instar larvae of *P. xylostella* were released. The petri dish was left to stand in a thermostatic chamber at a temperature of 25° C. and a humidity of 60% during the test period. Mortality was evaluated when 3 days passed since the release of the insects, and the insecticidal rate was calculated. The test was repeated twice.

The compounds with compound numbers shown in Table 7 were tested for efficacy against *P. xylostella*. All compounds showed an insecticidal rate of 80% or more against *P. xylostella*. The insecticidal rate of the comparative compound A was 0%.

TABLE 7

| Compound No. |
| --- |
| a-1 |
| a-4 |
| a-7 |
| a-8 |
| a-9 |
| a-10 |
| a-11 |
| a-12 |
| a-13 |
| a-15 |
| a-16 |
| a-17 |
| a-18 |
| a-19 |
| a-20 |
| a-24 |
| a-25 |
| a-26 |
| a-27 |
| a-28 |
| a-30 |
| a-32 |

TABLE 7-continued

| Compound No. |
| --- |
| a-33 |
| a-34 |
| a-36 |
| a-37 |
| a-38 |
| a-39 |
| a-40 |
| a-42 |
| a-43 |
| a-44 |
| a-45 |
| a-46 |
| a-47 |
| a-49 |
| a-50 |
| a-51 |
| a-52 |
| a-53 |
| a-59 |
| a-60 |
| a-61 |
| a-63 |
| a-65 |
| a-67 |
| a-68 |
| a-69 |
| a-73 |
| b-4 |
| b-5 |
| b-7 |
| b-8 |
| b-9 |
| b-10 |
| b-11 |
| b-12 |
| b-13 |
| b-14 |
| b-15 |
| b-16 |
| b-17 |
| b-18 |
| b-19 |
| b-20 |
| b-21 |
| c-1 |
| c-2 |
| c-3 |
| c-4 |
| c-6 |
| c-7 |
| c-8 |
| c-11 |
| c-12 |

(Test Example 4) Efficacy Test Against *Tetranychus urticae*

Kidney bean plants were raised in No. 3 pots, and 8 adult females of *T. urticae* from Aomori Prefecture were inoculated on primary leaves. The emulsion (I) was diluted with water so that the concentration of the compound of the present invention was 125 ppm. The diluent was sprayed on the kidney bean plants (treated group).

On the same day, the emulsion (11) was diluted 400 times with water. The diluent was sprayed on the kidney bean plants (untreated group).

The above No. 3 pots were left to stand in a thermostatic chamber at a temperature of 25° C. and a humidity of 65% during the test period. The inoculated adult females of *T. urticae* were removed with an aspirator 3 days after spraying. Eggs were laid on the leaves. The number of surviving individuals was examined 10 days after spraying, and the control rate was calculated according to the following formula. The test was repeated twice.

Control rate (%)=100×[1−Nt/Nc]

Nt: number of surviving individuals in treated group, Nc: number of surviving individuals in untreated group The compounds with compound numbers shown in Table 8 were tested for efficacy against *T. urticae*. All compounds showed a control rate of 90% or more. The control rate of the comparative compound A was 100%.

TABLE 8

| Compound No. |
|---|
| a-1 |
| a-4 |
| a-7 |
| a-8 |
| a-9 |
| a-10 |
| a-15 |
| a-16 |
| a-17 |
| a-20 |
| a-27 |
| a-28 |
| a-30 |
| a-32 |
| a-33 |
| a-34 |
| a-36 |
| a-37 |
| a-38 |
| a-39 |
| a-41 |
| a-42 |
| a-43 |
| a-44 |
| a-49 |
| a-50 |
| a-51 |
| a-52 |
| a-53 |
| a-57 |
| a-59 |
| a-60 |
| a-61 |
| a-63 |
| a-65 |
| a-68 |
| a-69 |
| a-71 |
| b-11 |
| b-13 |
| b-15 |
| b-17 |
| b-20 |
| b-21 |
| c-1 |
| c-2 |
| c-3 |
| c-4 |
| c-7 |
| c-8 |
| c-11 |
| c-12 |

(Test Example 5) Efficacy Test Against *Thrips palmi*

1% agar was poured into a plastic petri dish (90 mm diameter), and a primary leaf piece of a kidney bean plant was placed thereon. 15 first instar larvae of *T. palmi* were inoculated thereon. The emulsion (I) was diluted with water so that the concentration of the compound of the present invention was 125 ppm. The diluent was sprayed on the leaf piece of the kidney bean plant. The petri dish was left to stand in a thermostatic chamber at a temperature of 25° C. and a humidity of 60% during the test period. Mortality of *T. palmi* was examined 2 days after that, and the insecticidal rate was calculated. The test was repeated twice.

The compounds with compound numbers shown in Table 9 were tested for efficacy against *T. palmi* at a compound concentration of 125 ppm. All compounds showed an insecticidal rate of 80% or more. The insecticidal rate of the comparative compound A was 0%.

TABLE 9

| Compound No. |
|---|
| a-52 |
| a-59 |
| a-104 |
| a-105 |
| b-20 |

(Test Example 6) Efficacy Test Against Diamide-Based Insecticide-Resistant *Plutella xylostella*

The emulsion (I) was diluted with water so that the concentration of the compound of the present invention was 125 ppm. Cabbage leaves were immersed in the diluent for 30 seconds. The cabbage leaves were air dried and placed in a petri dish, and five second instar larvae of diamide-based insecticide-resistant *P. xylostella* were released.

The petri dish was left to stand in a thermostatic chamber at a temperature of 25° C. and a humidity of 60% during the test period. Mortality was evaluated when 3 days passed since the release of the insects, and the insecticidal rate was calculated. The test was repeated twice.

The compounds with compound numbers shown in Table 10 were tested for efficacy against diamide-based insecticide-resistant *P. xylostella*. The compounds showed an insecticidal rate of 80% or more against diamide-based insecticide-resistant *P. xylostella*. The insecticidal rate of the comparative compound A was 0%. The insecticidal rate of a flubendiamide wettable powder (trade name: Phoenix granular wettable powder) at 50 ppm was 0%, which served as a control experiment.

TABLE 10

| Compound No. |
|---|
| a-1 |
| a-50 |
| a-51 |
| a-52 |
| a-59 |
| a-84 |
| a-90 |
| a-91 |
| a-92 |
| a-93 |
| a-94 |
| a-104 |
| a-105 |
| a-106 |
| a-108 |
| b-29 |
| b-30 |
| d-2 |

(Test Example 7) Efficacy Test Against Benzoylurea-Based Insecticide-Resistant *Helicoverpa armigera*

The emulsion (I) was diluted with water so that the concentration of the compound of the present invention was 125 ppm. Cabbage leaves were immersed in the diluent for 30 seconds. The cabbage leaves were air dried and placed in a petri dish, and 8 second instar larvae of benzoylurea-based insecticide-resistant *H. armigera* were inoculated.

The petri dish was left to stand in a thermostatic chamber at a temperature of 25° C. and a humidity of 60% during the test period. Mortality was evaluated when 3 days passed since the release of the insects, and the insecticidal rate was calculated. The test was repeated twice.

The compounds with compound numbers shown in Table 11 were tested for efficacy against benzoylurea-based insecticide-resistant *H. armigera*. The compounds showed an insecticidal rate of 80% or more against benzoylurea-based insecticide-resistant *H. armigera*. The insecticidal rate of the comparative compound A was 0%. The insecticidal rate of a teflubenzuron emulsion (trade name: Nomolt emulsion) at 25 ppm was 0%, which served as a control experiment.

TABLE 11

| Compound No. |
| --- |
| a-1 |
| a-50 |
| a-51 |
| a-52 |
| a-59 |
| a-75 |
| a-77 |
| a-78 |
| a-81 |
| a-82 |
| a-83 |
| a-84 |
| a-85 |
| a-91 |
| a-93 |
| a-94 |
| a-95 |
| a-96 |
| a-97 |
| a-98 |
| a-100 |
| a-101 |
| a-104 |
| a-105 |
| a-106 |
| a-111 |
| a-116 |
| a-117 |
| a-118 |
| a-119 |
| b-29 |
| b-30 |
| b-35 |
| c-3 |

(Test Example 8) Efficacy Test Against *Plutella xylostella* (Root Dipping Treatment Test)

Cabbages raised to 2 leaf stage were pulled out from the soil, and after washing off the soil attached to the roots with tap water, hydroponically cultivated for 4 days by soaking the roots in tap water. The emulsion (I) was diluted with water so that the concentration of the compound of the present invention was 7.8 ppm, thereby preparing a drug solution for the root dipping test. The hydroponic cultivation was continued in a thermostatic chamber at a temperature of 25° C. and a humidity of 60% with the roots of cabbage seedlings being soaked in the drug solution.

Four days after the start of hydroponic culture with the drug solution, the second true leaf and the third true leaf of cabbage were placed in a petri dish and inoculated with the second instar larvae of *P. xylostella*.

The petri dish was left to stand in a thermostatic chamber at a temperature of 25° C. and a humidity of 60% during the test period. Mortality was evaluated after 3 days, and the insecticidal rate was calculated. The test was repeated twice.

The compounds with compound numbers shown in Table 12 were tested for efficacy against *P. xylostella* by the root dipping treatment. All compounds showed an insecticidal rate of 80% or more against *P. xylostella* by the root dipping treatment.

TABLE 12

| Compound No. |
| --- |
| a-9 |
| a-26 |
| a-27 |
| a-30 |
| a-32 |
| a-34 |
| a-36 |
| a-37 |
| a-39 |
| a-59 |
| a-61 |
| a-65 |
| a-68 |
| a-69 |
| a-70 |
| a-73 |
| b-17 |
| b-21 |
| c-3 |
| c-4 |
| c-6 |
| c-7 |
| c-12 |

Since those randomly selected from among the pyridinium salts of the present invention exert the above-mentioned effects, it can be understood that the pyridinium salts of the present invention including the compounds that are not shown in examples are compounds having the effects of pest control, acaricidal effects, and in particular, insecticidal effects and the like.

INDUSTRIAL APPLICABILITY

It is possible to provide a pyridinium salt which is excellent in pest control activity, in particular, insecticidal activity and/or acaricidal activity, excellent in safety and can be synthesized in an industrially favorable manner. In addition, it is possible to provide a pest control agent, an insecticidal or acaricidal agent, an ectoparasite control agent, or an endoparasite control- or exterminating agent containing a pyridinium salt as an active ingredient.

What is claimed is:

1. A compound represented by formula (I-a) or formula (II-a):

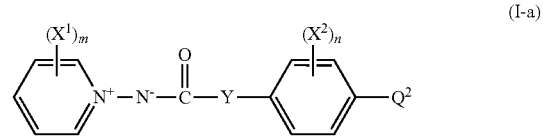

-continued

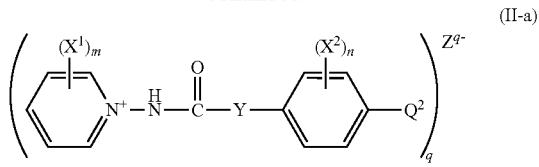
(II-a)

wherein:
X¹ represents a halogeno group, a halogeno group-substituted or unsubstituted $C_{1-6}$ alkyl group, or a halageno group-substituted or unsubstituted $C_{1-6}$ alkoxy group;
m represents the number of X¹ and is any integer of 0 to 5;
any two of X¹ may be bound together to form a bivalent hydrocarbon group;
Y represents a single bond or a substituted or unsubstituted $C_{2-6}$ alkenylene group, wherein the substituent on the $C_{2-6}$ alkenylene group represented by Y is a halogeno group, a halogeno group-substituted or unsubstituted $C_{1-6}$ alkyl group, a halogeno group-substituted or unsubstituted $C_{1-6}$ alkoxy group, a $C_{1-6}$ alkylthio group, a $C_{1-6}$ alkylsulfinyl group, or a $C_{1-6}$ alkyl sulfonyl group;
X² represents a halogeno group, a halogeno group-substituted or unsubstituted $C_{1-6}$ alkyl group, a halogeno-substituted or unsubstituted $C_{1-6}$ alkoxy group, or a nitro group;
n represents the number of X² and is any integer of 0 to 2;
Q² represents a substituted or unsubstituted $C_{6-10}$ aryl group or a substituted or unsubstituted 5- to 6-membered heteroaryl group, wherein the substituent on the $C_{6-10}$ aryl group or 5- to 6-membered heteroaryl group represented by Q² is a halogeno group, a halogeno group-substituted or unsubstituted $C_{1-6}$ alkyl group, a halogeno group-substituted or unsubstituted $C_{2-6}$ alkynyl group, a hydroxyl group, a halogeno group-substituted or unsubstituted $C_{1-6}$ alkoxy group, a substituted or unsubstituted benzyl group, a halogeno group-substituted or unsubstituted $C_{1-6}$ alkoxycarbonyl group, a halogeno group-substituted or unsubstituted $C_{1-6}$ alkylthio group, a halogeno group-substituted or unsubstituted $C_{1-6}$ alkylsulfonyl group, a halogeno group-substituted or unsubstituted $C_{1-6}$ alkylsulfonyloxy group, a di $C_{1-6}$ alkylamino group, a halogeno group-substituted or unsubstituted $C_{3-8}$ cycloalkyl group, a halogeno group-substituted or unsubstituted $C_{3-8}$ cycloalkyloxy group, a substituted or unsubstituted phenyl group, a pentafluorosulfanyl group, or a cyano group;
$Z^{q-}$ represents a counter ion;
q represents a valence of the counter ion and is 1 or 2; and
"substituted" means that any hydrogen atom of the group which is to become the mother nucleus is substituted with a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a $C_{6-10}$ aryl $C_{1-6}$ alkyl group, a 3- to 6-membered heterocyclyl group, a 3- to 6-membered heterocyclyl $C_{1-6}$ alkyl group, a hydroxyl group, a $C_{1-6}$ alkoxy group, a $C_{2-6}$ alkenyloxy group, a $C_{2-6}$ alkynyloxy group, a $C_{6-10}$ aryloxy group, a $C_{6-10}$ aryl $C_{1-6}$ alkoxy group, a 5- to 6-membered heteroaryloxy group, a 5- to 6-membered heteroaryl $C_{1-6}$ alkyloxy group, a formyl group, a $C_{1-6}$ alkylcarbonyl group, a formyloxy group, a $C_{1-6}$ alkylcarbonyloxy group, a $C_{6-10}$ arylcarbonyl group, a $C_{1-6}$ alkoxycarbonyl, a $C_{1-6}$ alkoxycarbonyloxy group, a carboxyl group, a halogeno group, a $C_{1-6}$ haloalkyl group, a $C_{2-6}$ haloalkenyl group, a $C_{2-6}$ haloalkynyl group, a $C_{1-6}$ haloalkoxy group, a $C_{2-6}$ haloalkenyloxy group, a $C_{1-6}$ haloalkylcarbonyl group, an amino group, a $C_{1-6}$ alkyl-substituted amino group, a $C_{6-10}$ arylamino group, a $C_{6-10}$ aryl $C_{1-6}$ alkylamino group, a formylamino group, a $C_{1-6}$ alkylcarbonylamino group, a $C_{1-6}$ alkoxycarbonylamino group, an aminocarbonyl group, a dimethylaminocarbonyl group, a phenylaminocarbonyl group, an N-phenyl-N-methylaminocarbonyl group, an imino $C_{1-6}$ alkyl group, an N-hydroxy-iminomethyl group, a (1-(N-hydroxy)-imino)ethyl group, a (1-(N-hydroxy)-imino)propyl group, an N-methoxy-iminomethyl group, a (1-(N-methoxy)-imino)ethyl group, an aminocarbonyloxy group, a $C_{1-6}$ alkyl-substituted aminocarbonyloxy group, a mercapto group, a $C_{1-6}$ alkylthio group, a $C_{1-6}$ haloalkylthio group, a $C_{6-10}$ arylthio group, a 5- to 6-membered heteroarylthio group, a $C_{1-6}$ alkylsulfinyl group, a $C_{1-6}$ haloalkylsulfinyl group, a $C_{6-10}$ arylsulfinyl group, a 5- to 6-membered heteroarylsulfinyl group, a $C_{1-6}$ alkylsulfonyl group, a $C_{1-6}$ haloalkylsulfonyl group, a $C_{6-10}$ arylsulfonyl group, a 5- to 6-membered heteroarylsulfonyl group, a $C_{1-6}$ alkylsulfonyloxy group, a $C_{1-6}$ haloalkylsulfonyloxy group, a tri $C_{1-6}$ alkyl-substituted silyl group, a tri $C_{6-10}$ aryl-substituted silyl group, a pentafluorosulfanyl group, a cyano group, or a nitro group.

2. A composition that is a pest control agent, insecticidal agent, acaricidal agent, ectoparasite control agent, endoparasite control agent, or exterminating agent, comprising:
at least one compound selected from the compounds according to claim 1 as an active ingredient; and
a carrier,
wherein the composition is formulated as a tablet, capsule, mixed feed, wettable powder, emulsion, granule, suspension, injectable composition, pour-on composition, spot-on composition, spray, aqueous composition, oily composition, immersion liquid, or suppository.

3. The composition of claim 2, wherein the composition is an ectoparasite control agent formulated as a tablet, capsule, mixed feed, immersion liquid, suppository, injection, or spray.

4. The composition of claim 2, wherein the composition is a pest control agent and further comprises one or more fungicides, insecticidal agents, aricidal agents, nematicides, soil pesticides, plant growth regulators, synergists, fertilizers, soil conditioners, or animal feeds.

5. The composition of claim 2, wherein the composition is an ectoparasite control agent formulated for topical, oral, parenteral, or subcutaneous administration to an animal.

* * * * *